(12) United States Patent
Lu et al.

(10) Patent No.: US 7,833,541 B2
(45) Date of Patent: *Nov. 16, 2010

(54) COSMETIC COMPOSITIONS UTILIZING ACRYLATE CROSS LINKED SILICONE COPOLYMER NETWORKS

(75) Inventors: Ning Lu, White Plains, NY (US); Anna Maria Czech, Bronxville, NY (US); Pat Hoontrakul, Murfreesboro, TN (US); John Nicholson, Ramsey, NJ (US); Roy Rojas-Wahl, Teaneck, NJ (US)

(73) Assignee: Momentive Performance Materials Inc., Albany, NY (US)

( * ) Notice: Subject to any disclaimer, the term of this patent is extended or adjusted under 35 U.S.C. 154(b) by 581 days.

This patent is subject to a terminal disclaimer.

(21) Appl. No.: 11/742,190

(22) Filed: Apr. 30, 2007

(65) Prior Publication Data

US 2008/0009600 A1    Jan. 10, 2008

Related U.S. Application Data

(60) Provisional application No. 60/746,079, filed on May 1, 2006.

(51) Int. Cl.
*A61K 8/04* (2006.01)
(52) U.S. Cl. ............................ 424/401; 528/25; 528/26; 528/27; 528/31
(58) Field of Classification Search ................ None
See application file for complete search history.

(56) References Cited

U.S. PATENT DOCUMENTS

| | | | |
|---|---|---|---|
| 4,293,678 A | 10/1981 | Carter et al. | |
| 4,663,185 A * | 5/1987 | Eckberg | ..................... 427/503 |
| 4,987,169 A | 1/1991 | Kuwata et al. | |
| 5,039,761 A | 8/1991 | Ono et al. | |
| 5,156,575 A | 10/1992 | Czech | |
| 5,204,433 A * | 4/1993 | Wewers et al. | ................. 528/12 |
| 5,493,041 A | 2/1996 | Biggs et al. | |
| 5,550,270 A * | 8/1996 | Takarada et al. | ............. 556/440 |
| 5,760,116 A | 6/1998 | Kilgour | |
| 6,207,782 B1 | 3/2001 | Czech | |
| 6,313,249 B1 | 11/2001 | Nakanishi | |
| 6,399,081 B1 | 6/2002 | Nakanishi | |
| 6,448,361 B1 * | 9/2002 | Austin et al. | ................... 528/25 |
| 2002/0002114 A1 | 1/2002 | Policello et al. | |
| 2002/0035229 A1 * | 3/2002 | Kondo et al. | ................... 528/10 |
| 2002/0159964 A1 * | 10/2002 | Nakanishi et al. | ......... 424/70.12 |
| 2004/0213945 A1 * | 10/2004 | Patel et al. | ................. 428/40.1 |
| 2007/0149723 A1 * | 6/2007 | Schwab | ...................... 525/479 |
| 2007/0207176 A1 * | 9/2007 | Kamei et al. | ................. 424/401 |

FOREIGN PATENT DOCUMENTS

| | | |
|---|---|---|
| DE | 43 00 267 C1 | 4/1994 |
| EP | 1 000 959 A2 | 5/2000 |

OTHER PUBLICATIONS

Abstract for JP 52-27898.*
Ichiro Ono Allured, Development of new cosmetic silicones for foundation formulations, Cosmetics & Toiletries Magazine, vol. 116, No. 3/Mar. 2001.
M. Mazurek, D.J. Dinning, T. Kinoshita, Novel materials based on silicone-acrylate copolymer networks, Journal of Applied Polymer Science vol. 80, Issue 2, 159-180.
Park, Hong-Soo; Yang, In-Mo; Wu, Jong-Pyo; Kim, Myung-Soo; Hahm, Hyun-Sik; Kim, Seong-Kil; Rhee, Hee-Woo, Synthesis of silicone-acrylate resins and their applications to superweatherable coatings, Journal of Applied Polymer Science (2001), 81(7), 1614-1623.

* cited by examiner

*Primary Examiner*—Marc S Zimmer
(74) *Attorney, Agent, or Firm*—Kenneth S. Wheelock

(57) ABSTRACT

The cosmetic compositions of the present invention comprise silicone copolymers, terpolymers and higher order polymers that comprise 1) polyether substituted structural units and 2) epoxy or oxirane structural units that are reacted with acrylate species to produce cross linked silicones comprising polyether substituted structural units and acrylate cross links. The cross linked polymers of the present invention are self-emulsifying and may be either water swellable or oil swellable.

54 Claims, No Drawings

COSMETIC COMPOSITIONS UTILIZING ACRYLATE CROSS LINKED SILICONE COPOLYMER NETWORKS

CROSS-REFERENCE TO RELATED APPLICATIONS

This application claims the benefit of U.S. Provisional Application Ser. No. 60/746,079, filed May 1, 2006

FIELD OF THE INVENTION

The present invention relates to compositions comprising cross linked silicone copolymer networks where the cross links are acrylate oligomers or polymers, methods of making the compositions and uses for the compositions.

BACKGROUND OF THE INVENTION

The personal care industry thrives on being able to deliver multiple performance products based on mixtures of several components, with each having performance characteristics important to or desirable in the final formulation. One desirable characteristic is the ability to provide a silky initial feel derived from low molecular weight silicones, such as for example, octamethylcyclotetrasilioxane or decamethylcyclopentasiloxane, in the formulation while maintaining a high, but shear-thinnable viscosity. While these low molecular weight silicones provide the desired feel characteristics, they are also low viscosity, highly flowable liquids. Thus they are not easily held in a formulation, preferring rather to separate and flow out of a given container or flow uncontrollably across the skin when used in a specific application. Further, it desirable to achieve an initial silky feel while providing a smooth, low-residue feel upon dry-down. Polymeric silicone gels prepared in volatile silicone have been found to deliver desirable initial feel of volatile, low viscosity silicones to formulations while at the same time provide high viscosity and a smooth silky feel on dry-down, see for example, U.S. Pat. Nos. 5,760,116, 5,493,041 and 4,987,169.

Such polymeric silicone gels have typically been made by the hydrosilylation reaction, which requires the use of both SiH functional groups and terminal olefinic groups to form crosslinked siloxane polymers. Thus only siloxane structures that can incorporate silylhydride groups and optionally, vinyl functional siloxane groups, can be utilized in making these materials. Further this method of generating crosslinked siloxane polymers limits the range of desirable organofunctional groups that may be incorporated into the polymeric structure to create additional performance advantages in complex formulations. Thus attempts to include organofunctional groups into the crosslinked siloxane polymer include unsaturated organic groups compatible with the hydrosilylaton reaction.

U.S. Pat. Nos. 6,313,249; 6,399,081; and 5,039,761 disclose a method for the preparation of a silicone-grafted acrylic copolymer that consists of an acrylic backbone and a polysiloxane side chain. U.S. Pat. No. 6,207,782) discloses free-radical polymerized acrylates/methacrylates of polyether-terminated polysiloxanes and emulsions including these polymers. U.S. Pat. No. 4,293,678) discloses a class of materials termed acrylated epoxy silicones that are made from an epoxy silicone and acrylic acid which include a polyether-substituted silicone.

Silicone network polymers are widely used as components of various personal care compositions. However, most of these silicone network polymers are not compatible with polar media such as water. Therefore, there is a need in personal care for hydrophilic silicone networks that are compatible with a wide range of polar or non-polar media and which can provide performance benefits such as emulsification, thickening, adhesion, gloss, durability and detackification of hydrophilic actives.

SUMMARY OF THE INVENTION

The present invention provides for a method of making a cosmetic composition comprising a silicone composition, the cosmetic silicone composition and uses thereof comprising the reaction product of:

a) $M_a M^H_{b-h-k} M^{PE}_h M^E_k D_c D^H_{d-i-l} D^{PE}_i D^E_l T_e T^H_{f-j-m} T^{PE}_j T^E_m Q_g$ and b) a stoichiometric or super-stoichiometric quantity of acrylate where $M = R^1 R^2 R^3 SiO_{1/2}$;

$M^H = R^4 R^5 HSiO_{1/2}$;

$M^{PE} = R^4 R^5 (-CH_2 CH(R^9)(R^{10})_n O(R^{11})_o (C_2 H_4 O)_p (C_3 H_6 O)_q (C_4 H_8 O)_r R^{12}) SiO_{1/2}$;

$M^E = R^4 R^5 (-R^{17} R^{18} C - CR^{16} Q_s Q_r R^{15} (COC) R^{13} R^{14}) SiO_{1/2}$ $D = R^6 R^7 SiO_{2/2}$; and $D^H = R^8 HSiO_{2/2}$ $D^{PE} = R^8 (-CH_2 CH(R^9)(R^{10})_n O(R^{11})_o (C_2 H_4 O)_p (C_3 H_6 O)_q (C_4 H_8 O)_r R^{12}) SiO_{2/2}$ $D^E = R^8 (-R^{17} R^{18} C - CR^{16} Q_s Q_r R^{15} (COC) R^{13} R^{14}) SiO_{2/2}$.

$T = R^{19} SiO_{3/2}$;

$T^H = HSiO_{3/2}$;

$T^{PE} = (-CH_2 CH(R^9)(R^{10})_n O(R^{11})_o (C_2 H_4 O)_p (C_3 H_6 O)_q (C_4 H_8 O)_r R^{12}) SiO_{3/2}$;

$T^E = (-R^{17} R^{18} C - CR^{16} Q_s Q_r R^{15} (COC) R^{13} R^{14}) SiO_{3/2}$; and $Q = SiO_{4/2}$;

where $R^1$, $R^2$, $R^3 R^4$, $R^5$, $R^6$, $R^7$, $R^8$ and $R^{19}$ are each independently selected from the group of monovalent hydrocarbon radicals having from 1 to 60 carbon atoms;

$R^9$ is H or a 1 to 6 carbon atom alkyl group; $R^{10}$ is a divalent alkyl radical of 1 to 6 carbons;

$R^{11}$ is selected from the group of divalent radicals consisting of $-C_2 H_4 O-$, $-C_3 H_6 O-$, and $-C_4 H_8 O-$; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q^s$ is a divalent hydrocarbon radical having from one to sixty carbon atoms subject to the limitation that when $Q_t$ is trivalent $R^{14}$ is absent and $R^{16}$ and $R^{18}$ may be either cis- or trans- to each other;

the subscript a may be zero or positive subject to the limitation that when the subscript a is zero, b must be positive;

the subscript b may be zero or positive subject to the limitation that when b is zero, the subscript a must be positive;

the subscript c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2 subject to the limitation that the sum of the subscripts h, i and j is positive;

the subscript i is zero or positive and has a value ranging from 0 to about 200 subject to the limitation that the sum of the subscripts h, i and j is positive;

the subscript j is zero or positive and has a value ranging from 0 to about 30 subject to the limitation that the sum of the subscripts h, i and j is positive;

the subscript k is zero or positive and has a value ranging from 0 to about 2 subject to the limitation that the sum of the subscripts k, l and m is positive;

the subscript l is zero or positive and has a value ranging from 0 to about 200 subject to the limitation that the sum of the subscripts k, l and m is positive;

the subscript m is zero or positive and has a value ranging from 0 to about 30 subject to the limitation that the sum of the subscripts k, l and m is positive;

the subscript n is zero or one;

the subscript o is zero or one;

the subscript p is zero or positive and has a value ranging from 0 to about 100 subject to the limitation that (p+q+r)>0;

the subscript q is zero or positive and has a value ranging from 0 to about 100 subject to the limitation that (p+q+r)>0;

the subscript r is zero or positive and has a value ranging from 0 to about 100 subject to the limitation that (p+q+r)>0;

the subscript s is zero or one;

the subscript t is zero or one; and c) a free radical initiator.

DETAILED DESCRIPTION OF THE INVENTION

As used herein, integer values of stoichiometric subscripts refer to molecular species and non-integer values of stoichiometric subscripts refer to a mixture of molecular species on a molecular weight average basis, a number average basis or a mole fraction basis. The phrases sub-stoichiometric and super stoichiometric refer to relationships between reactants. Sub stoichiometric refers to a quantity of reactant that is less than the quantity of reactant required for full stoichiometric reaction of a substrate moiety with that reactant. Super stoichiometric refers to a quantity of reactant that is more than that quantity of reactant required for full stoichiometric reaction of a substrate moiety with that reactant. As used herein "super stoichiometric" can under some circumstances be equivalent to an excess that is either a stoichiometric excess, i.e. a whole number multiple of a stoichiometric quantity, or a non-stoichiometric excess.

The present invention provides for a method of making the compositions of the present invention, compositions and useful compositions comprising the composition of the invention.

The method of the present invention provides for reacting a silyl hydride copolymer with sub-stoichiometric quantities of an olefinic polyether under hydrosilylation conditions to yield a polyether substituted hydride terpolymer.

Thus in one specific embodiment, the process of the invention leading to compositions of the invention is as follows, a silyl hydride having the formula:

$$M_a M^H_b D_c D^H_d,$$

where $M = R^1 R^2 R^3 SiO_{1/2}$;
$M^H = R^4 R^5 HSiO_{1/2}$;
$D = R^6 R^7 SiO_{2/2}$; and
$D^H = R^8 HSiO_{2/2}$ with $R^1$, $R^2$, $R^3$, $R^4$, $R^5$, $R^6$, $R^7$, $R^8$ and $R^{19}$ are each independently selected from the group of monovalent hydrocarbon radicals having from 1 to 60 carbon atoms, where the subscripts a, b, c and d are zero or positive; is reacted under hydrosilylation conditions with a sub-stoichiometric quantity, i.e. a molar quantity that is less than the molar quantity equivalent to the sums of the subscripts b and d; that quantity being the sum of stoichiometric subscripts h and i, of an olefinic polyether having the formula:

$$CH_2=CH(R^9)(R^{10})_n O(R^{11})_o (C_2H_4O)_p (C_3H_6O)_q (C_4H_8O)_r R^{12}$$

where $R^9$ is H or a 1 to 6 carbon atom alkyl group; $R^{10}$ is a divalent alkyl radical of 1 to 6 carbons where the subscript n may be 0 or 1; $R^{11}$ is selected from the group of divalent radicals consisting of $—C_2H_4O—$, $—C_3H_6O—$, and $—C_4H_8O—$ where the subscript o may be 0 or 1; $R^{12}$ is H, a monofunctional hydrocarbon radical of 1 to 6 carbons, or acetyl and the subscripts p, q and r are zero or positive. When the polyether is composed of mixed oxyalkyleneoxide groups (i.e. oxyethylene, oxypropylene and oxybutylene) the units may be blocked, or randomly distributed. The resulting terpolymer has a formula consistent with the formula:

$$M_a M^H_{b-h} M^{PE}_e D_c D^H_{d-i} D^{PE}_f$$

where the superscript PE indicates polyether substitution, with $M^{PE} = R^4 R^5 (—CH_2 CH(R^9)(R^{10})_n O(R^{11})_o (C_2H_4O)_p (C_3H_6O)_q (C_4H_8O)_r R^{12}) SiO_{1/2}$ and $D^{PE} = R^8 (—CH_2 CH(R^9)(R^{10})_n O(R^{11})_o (C_2H_4O)_p (C_3H_6O)_q (C_4H_8O)_r R^{12}) SiO_{2/2}$ This terpolymer is further reacted under hydrosilylation conditions with a sub-stoichiometric quantity, i.e. a molar quantity that is less than the molar quantity equivalent to the sums of the subscripts (b-h) and (d-i); that quantity being the sum of stoichiometric subscripts k and l, of an olefinic epoxide or oxirane having the formula:

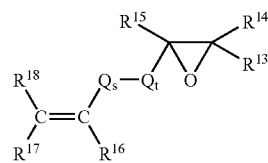

which is $R^{17} R^{18} C=CR^{16} Q_s Q_t R^{15} (COC) R^{13} R^{14}$ where $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q_s$ is a divalent hydrocarbon radical having from one to sixty carbon atoms with the subscripts s and t independently zero or one subject to the limitation that when $Q_t$ is trivalent $R^{14}$ is absent and $R^{16}$ and $R^{18}$ may be either cis- or trans- to each other. The resulting polymer has a formula consistent with:

$$M_a M^H_{b-h-k} M^{PE}_e M^E_g D_c D^H_{d-i-l} D^{PE}_f D^E_j,$$

where the superscript E indicates epoxide or oxirane substitution, with $M^E = R^4 R^5 (—R^{17} R^{18} C—CR^{16} Q_s Q_t R^{15} (COC) R^{13} R^{14}) SiO_{1/2}$ and $D^E = R^8 (—R^{17} R^{18} C—CR^{16} Q_s Q_t R^{15} (COC) R^{13} R^{14}) SiO_{2/2}.$ When the residual hydride is greater than zero, as indicated by non-zero values for stoichiometric quantities of (b-h-k) and (d-i-l), further hydrosilylation reactions with various olefinic species including alkenyl silicone resins may be conducted to create higher order polymers. It should be noted that the sequence of hydrosilylation reactions described may be reversed or they may be combined and accomplished in one reaction.

The polymer having the formula:

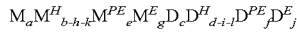

is further reacted with acrylic acid, a substituted acrylic acid or esters thereof to provide an acrylate ester of the epoxide or oxirane functional group, providing the acrylate ester polymer having a formula:

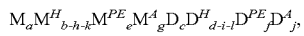

where the superscript a is indicative of and denotes a substituent that is the reaction product between the epoxy substituent: $(-R^{17}R^{18}C-CR^{16}Q_sQ_tR^{15}(COC)R^{13}R^{14})$ and an acrylate species. Addition of excess acrylate species along with a free radical initiator generates polyacrylate cross links. The acrylated polyether-grafted polysiloxane copolymer may be polymerized or copolymerized with one or more comonomers, under free radical polymerization conditions, which polymerization may be conducted in various solvents, using catalysts and temperatures as are known in the art for polymerizing acrylates. Suitable solvents include but are not limited to silicone fluid, water, alcohol, ester, hydrocarbon fluid or organic oil. Examples of free radical initiating catalysts (hereinafter free radical initiator) include: inorganic peroxides such as hydrogen peroxide, ammonium persulfate, potassium persulfate and the like; organic peroxy catalysts, such as dialkyl peroxides, e.g., diisopropyl peroxide, dilauryl peroxide, di-t-butyl peroxide, dicumyl peroxide, alkyl hydrogen peroxides such as t-butyl hydrogen peroxide, t-amyl hydrogen peroxide, cumyl hydrogen peroxide, diacyl peroxide, for instance acetyl peroxide, lauroyl peroxide, benzoyl peroxide, peroxy ester such as ethyl peroxybenzoate, pavalate peroxide, the azo compounds such as 2-azobis(isobutyronitrile), 1-azobis(1-cyclohexanecarbonitrile) and the like and other free radical generating catalysts.

Thus in one embodiment the compositions of the present invention are the reaction product between polymers having the formula:

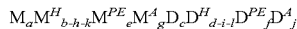

and acrylate species.

More generally any hydride bearing silicone polymer maybe subjected to this reaction scheme to produce epoxy substituted, polyether substituted silicone polymers that may then be reacted with acrylic acid, substituted acrylic acid or its derivatives to produce acrylate cross-linked polyether substituted silicone polymer networks. The epoxy substituted polyether-grafted polysiloxane copolymer having the formula:

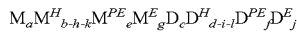

is reacted with an acrylate, usually acrylic acid or methacrylic acid to form an acrylated polyether-grafted polysiloxane copolymer. The epoxy ring opening reaction with acrylate will proceed uncatalyzed but a catalyst may be employed. Examples of useful catalysts include 1,4-Diazabicyclo(2.2.2) octane, aluminum chloride, titanium tetra(isopropoxide), p-toluene sulfonic acid, methane sulfonic acid, trifluoroacetic acid, morpholine tributylamine, benzoyldimethy amine, tetraalkylurea compounds such as 1,1',3,3'-tetramethylurea.

More generally the process of the present invention leading to compositions of the present invention comprises reacting a silicone hydride having the formula:

under hydrosilylation conditions with a sub-stoichiometric quantity of an olefinic polyether, that sub-stoichiometric molar quantity represented by the sum (h+i+j) to yield a polyether substituted polymer having a formula consistent with:

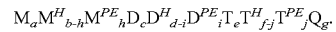

The polyether substituted polymer having the formula:

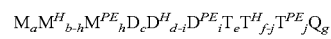

is subsequently reacted under hydrosilylation conditions with a sub-stoichiometric quantity of an olefinic epoxide or oxirane, that sub-stoichiometric molar quantity represented by the sum (k+l+m), to yield an epoxy and polyether substituted polymer having a formula consistent with:

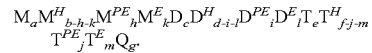

Reaction of

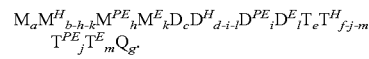

with acrylate functional compounds creates the correspond acrylate esters of the epoxy or oxirane groups leading to a silicone polymer having the following formula:

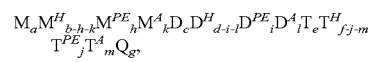

where the superscript A is indicative of and denotes a substituent that is the reaction product between the epoxy substituent: $(-R^{17}R^{18}C-CR^{16}Q_sQ_tR^{15}(COC)R^{13}R^{14})$ and an acrylate species. The epoxy substituted polyether-grafted polysiloxane copolymer having the formula:

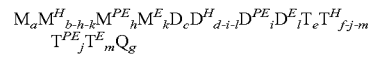

is reacted with an acrylate, usually acrylic acid or methacrylic acid to form an acrylated polyether-grafted polysiloxane copolymer. The epoxy ring opening reaction with acrylate will proceed uncatalyzed but a catalyst may be employed. Examples of useful catalysts include 1,4-Diazabicyclo(2.2.2) octane, aluminum chloride, titanium tetra(isopropoxide), p-toluene sulfonic acid, methane sulfonic acid, trifluoroacetic acid, morpholine tributylamine, benzoyldimethy amine, tetraalkylurea compounds such as 1,1',3,3'-tetramethylurea.

The polymer

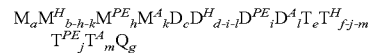

may then be further reacted with an additional quantity of an acrylate species or mixture thereof under conditions suitable to polymerize the acrylate components thereby generating acrylate oligomeric or polymeric cross links between the precursor $M_aM^H{}_{b-h-k}M^{PE}{}_hM^A{}_kD_cD^H{}_{d-i-l}D^{PE}{}_iD^A{}_lT_eT^H{}_{f-j-m}T^{PE}{}_jT^A{}_mQ_g$ polymer. These two steps may combined by utilizing either a stoichiometric or super stoichiometric amount of acrylate.

The compositions of the present invention include:

$$M_a M^H_{b-h-k} M^{PE}_h M^E_k D_c D^H_{d-i-l} D^{PE}_i D^E_l T_e T^H_{f-j-m} T^{PE}_j T^E_m Q_g;$$

$$M_a M^H_{b-h-k} M^{PE}_h M^A_k D_c D^H_{d-i-l} D^{PE}_i D^A_l T_e T^H_{f-j-m} T^{PE}_j T^A_m Q_g;$$

and the reaction product of these compounds with acrylate components.

As used herein the word "acrylate" is a collective noun for the following chemical species: acrylic acid and methacrylic acid or ester derivatives thereof such as methyl, ethyl, butyl, amyl, 2-ethylhexyl, cyclohexyl, vinyl, allyl, hydroxyethyl, perfluoroethyl, isobornyl, phenoxyethyl, tetraethylene glycol, tripropylene glycol, trimethylolpropane, polyoxyalkylene, organic modified polysiloxane (for example, the acrylated hydrophilic polysiloxane used as the emulsion precursor in U.S. Pat. No. 6,207,782), anionic acrylates/methacrylates, such as sulfate, sulfonate or phosphate functionalized acrylate or mixtures thereof and any catalyst necessary for reaction with the epoxy or oxirane group. A single acrylate or various combinations of acrylates and methacrylates may be employed.

As used herein, integer values of stoichiometric subscripts refer to molecular species and non-integer values of stoichiometric subscripts refer to a mixture of molecular species on a molecular weight average basis, a number average basis or a mole fraction basis. In the case of mixtures of the compounds of the present invention, it should be readily apparent that the stoichiometric subscripts of mixtures will have average values for the subscripts that may be either integral or non-integral in contrast to those of pure compounds.

The present invention provides for a method of making a silicone composition, the silicone composition and uses thereof comprising the reaction product of:

a) $M_a M^H_{b-h-k} M^{PE}_h M^E_k D_c D^H_{d-i-l} D^{PE}_i D^E_l T_e T^H_{f-j-m} T^{PE}_j T^E_m Q_g$ and b) a stoichiometric or super-stoichiometric quantity of acrylate where $M = R^1 R^2 R^3 SiO_{1/2}$;
$M^H = R^4 R^5 H SiO_{1/2}$;
$M^{PE} = R^4 R^5 (-CH_2 CH(R^9)(R^{10})_n O(R^{11})_o (C_2 H_4 O)_p (C_3 H_6 O)_q (C_4 H_8 O)_r R^{12}) SiO_{1/2}$;
$M^E = R^4 R^5 (-R^{17} R^{18} C-CR^{16} Q_s Q_t R^{15} (COC) R^{13} R^{14}) SiO_{1/2}$
$D = R^6 R^7 SiO_{2/2}$; and
$D^H D = R^8 H SiO_{2/2}$
$D^{PE} = R^8 (-CH_2 CH(R^9)(R^{10})_n O(R^{11})_o (C_2 H_4 O)_p (C_3 H_6 O)_q (C_4 H_8 O)_r R^{12}) SiO_{2/2}$
$D^E = R^8 (-R^{17} R^{18} C-CR^{16} Q_s Q_t R^{15} (COC) R^{13} R^{14}) SiO_{2/2}$.
$T = R^{19} SiO_{3/2}$;
$T^H = H SiO_{3/2}$;
$T^{PE} = (-CH_2 CH(R^9)(R^{10})_n O(R^{11})_o (C_2 H_4 O)_p (C_3 H_6 O)_q (C_4 H_8 O)_r R^{12}) SiO_{3/2}$;
$T^E = (-R^{17} R^{18} C-CR^{16} Q_s Q_t R^{15} (COC) R^{13} R^{14}) SiO_{3/2}$; and
$Q = SiO_{4/2}$;

where $R^1, R^2, R^3, R^4, R^5, R^6, R^7, R^8$ and $R^{19}$ are each independently selected from the group of monovalent hydrocarbon radicals having from 1 to 60 carbon atoms;

$R^9$ is H or a 1 to 6 carbon atom alkyl group; $R^{10}$ is a divalent alkyl radical of 1 to 6 carbons;

$R^{11}$ is selected from the group of divalent radicals consisting of $-C_2 H_4 O-$, $-C_3 H_6 O-$, and $-C_4 H_8 O-$; $R^{12}$ is H, a monofunctional hydrocarbon radical of 1 to 6 carbons, or acetyl; $R^{13}, R^{14}, R^{15}, R^{16}, R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q^s$ is a divalent hydrocarbon radical having from one to sixty carbon atoms subject to the limitation that when $Q_t$ is trivalent $R^{14}$ is absent and $Q^s$ forms a bond with the carbon bearing $R^{13}$ where $R^{16}$ and $R^{18}$ may be either cis- or trans- to each other;

the subscript a may be zero or positive subject to the limitation that when the subscript a is zero, b must be positive;

the subscript b may be zero or positive subject to the limitation that when b is zero, the subscript a must be positive;

the subscript c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2 subject to the limitation that the sum of the subscripts h, i and j is positive;

the subscript i is zero or positive and has a value ranging from 0 to about 200 subject to the limitation that the sum of the subscripts h, i and j is positive;

the subscript j is zero or positive and has a value ranging from 0 to about 30 subject to the limitation that the sum of the subscripts h, i and j is positive;

the subscript k is zero or positive and has a value ranging from 0 to about 2 subject to the limitation that the sum of the subscripts k, l and m is positive;

the subscript l is zero or positive and has a value ranging from 0 to about 200 subject to the limitation that the sum of the subscripts k, l and m is positive;

the subscript m is zero or positive and has a value ranging from 0 to about 30 subject to the limitation that the sum of the subscripts k, l and m is positive;

the subscript n is zero or one;

the subscript o is zero or one;

the subscript p is zero or positive and has a value ranging from 0 to about 100 subject to the limitation that $(p+q+r)>0$;

the subscript q is zero or positive and has a value ranging from 0 to about 100 subject to the limitation that $(p+q+r)>0$;

the subscript r is zero or positive and has a value ranging from 0 to about 100 subject to the limitation that $(p+q+r)>0$;

the subscript s is zero or one;

the subscript t is zero or one; and c) a free radical initiator.

The subscript a may be zero or positive subject to the limitation that when the subscript a is zero, b must be positive. The subscript b may be zero or positive subject to the limitation that when b is zero, the subscript a must be positive. In all cases the sum $a+b \geq 2$, i.e. the sum of a and b must be two or greater, depending on the number of T and Q groups present. $M_a M^H_b D_c D^H_d T_e T^H_f Q_g$ is the starting material and $M_a M^H_{b-h-k} M^{PE}_h M^E_k D_c D^H_{d-i-l} D^{PE}_i D^E_l T_e T^H_{f-j-m} T^{PE}_j T^E_m Q_g$ is the polymeric material prior to reaction with acrylate and subsequent cross linking.

The subscript c, which refers to the quantity of original D units, is positive and has a value ranging from about 5 to about 1,000, specifically from about 10 to about 700, more specifically from about 30 to about 500, and most specifically from about 50 to about 300.

The subscript d, which refers to the quantity of original $D^H$ units, is positive and has a value ranging from about 3 to about 400, specifically from about 3 to about 300, more specifically from about 3 to about 175, and most specifically from about 3 to about 40.

The subscript e, which refers to the quantity of original T units, is zero or positive and has a value ranging from 0 to about 50, specifically from about 0 to about 35, more specifically from about 0 to about 20, and most specifically from about 0 to about 10.

The subscript f, which refers to the quantity of original $T^H$ units, is zero or positive and has a value ranging from 0 to about 30, specifically from about 0 to about 25, more specifically from about 0 to about 17, and most specifically from about 0 to about 10.

The subscript g, which refers to the quantity of original Q units, is zero or positive and has a value ranging from 0 to about 20, specifically from about 0 to about 17, more specifically from about 0 to about 13, and most specifically from about 0 to about 10.

The subscript h, which refers to the quantity of $M^{PE}$ units, is zero or positive and has a value ranging from 0 to about 2, and most specifically from about 0 to about 1, subject to the limitations that the sum of the subscripts h, i and j is positive, i.e. $(h+i+j) \geq 0$, and $(b+d+f) \geq (h+i+j)+(k+l+m)$.

The subscript i, which refers to the quantity of $D^{PE}$ units, is zero or positive and has a value ranging from 0 to about 200, specifically from about 0 to about 140, more specifically from about 0 to about 80, and most specifically from about 1 to about 30 subject to the limitations that the sum of the subscripts h, i and j is positive, i.e. $(h+i+j) \geq 0$, and $(b+d+f) \geq (h+i+j)+(k+l+m)$.

The subscript j, which refers to the quantity of $T^{PE}$ units, is zero or positive and has a value ranging from 0 to about 30, specifically from about 0 to about 24, more specifically from about 0 to about 18, and most specifically from about 0 to about 10 subject to the limitations that the sum of the subscripts h, i and j is positive, i.e. $(h+i+j) \geq 0$, and $(b+d+f) \geq (h+i+j)+(k+l+m)$.

The subscript k, which refers to the quantity of $M^E$ units, is zero or positive and has a value ranging from 0 to about 2, and most specifically from about 0 to about 1 subject to the limitations that the sum of the subscripts k, l and m is positive, i.e. $(k+l+m) \geq 0$, and $(b+d+f) \geq (h+i+j)+(k+l+m)$.

The subscript l, which refers to the quantity of $D^E$ units is zero or positive and has a value ranging from 0 to about 200, specifically from about 0 to about 140, more specifically from about 0 to about 90, and most specifically from about 2 to about 20 subject to the limitations that the sum of the subscripts k, l and m is positive, i.e. $(k+l+m) \geq 0$, and $(b+d+f) \geq (h+i+j)+(k+l+m)$.

The subscript m, which refers to the quantity of $T^E$ units, is zero or positive and has a value ranging from 0 to about 30, specifically from about 0 to about 23, more specifically from about 0 to about 16, and most specifically from about 0 to about 10 subject to the limitations that the sum of the subscripts k, l and m is positive, i.e. $(k+l+m) \geq 0$, and $(b+d+f) \geq (h+i+j)+(k+l+m)$.

For the olefinic polyether having the formula:

$$CH_2=CH(R^9)(R^{10})_n O(R^{11})_o (C_2H_4O)_p (C_3H_6O)_q (C_4H_8O)_r R^{12}$$

The subscript n is zero or one.
The subscript o is zero or one.
The subscript p is zero or positive and has a value ranging from 0 to about 100, specifically from about 0 to about 85, more specifically from about 0 to about 55, and most specifically from about 0 to about 40, subject to the limitation that $(p+q+r)>0$.

The subscript q is zero or positive and has a value ranging from 0 to about 100, specifically from about 0 to about 80, more specifically from about 0 to about 60, and most specifically from about 0 to about 40, subject to the limitation that $(p+q+r)>0$.

The subscript r is zero or positive and has a value ranging from 0 to about 100, specifically from about 0 to about 75, more specifically from about 0 to about 50, and most specifically from about 0 to about 40, subject to the limitation that $(p+q+r)>0$.

Depending on the relative amounts of D, $D^A$ and $D^{PE}$ groups in the final cross-linked copolymeric network composition, the cross-linked composition will be swellable by either 1) a hydroxylic solvent such as water, an alcohol, or a carboxylic acid or solvent mixture where an aqueous or non-aqueous hydroxylic solvent is a component or 2) a non-aqueous non-hydrophilic solvent that may either be a silicone or an organic solvent as hereinafter later defined, or mixtures containing such solvents. For purposes of this discussion only these two classes of cross-linked swellable network copolymers will be referred to as "water-swellable" or "oil-swellable" (the term oil swellable encompassing all swelling solvents not embraced by the term "water swellable"). Generally, water swellability is more likely to occur with cross-linked network copolymers where the following relationships obtain:

1) for the number of D groups present: about 5<number of D groups≤about 90;
2) for the number of $D^{PE}$ groups present: $D^{PE}$>about 5; and
3) the acrylate cross-links constituting at least about 5 weight percent or more of the non-swollen cross-linked polymer network.

In contrast, oil swellability is more likely to occur with cross-linked network copolymers where the following relationships obtain:

1) for the number of D groups present: about 90≤number of D groups;
2) for the number of $D^{PE}$ groups present: about 1<number of $D^{PE}$ groups≤about 7;
3) the acrylate cross-links constituting no more than about 10 weight percent or less of the non-swollen cross-linked polymer network.

It is to be emphasized that the preceding ranges of structural parameters and stoichiometric subscripts exemplified for water or oil swellability are variable and interdependent and each parametric variable may be exceeded by being greater than or less than the indicated ranges and still observing a particular type of swellability by reason of a homeostatic variation in another structural or stoichiometric parameter associated with the particular polymer.

Since both the acrylate cross-links and the polyether substituents are capable of hydrogen bonding with water and other hydroxylic solvents, increasing content of either, all other composition variables remaining constant, will tend to increase the water swellability of the resulting cross-linked network polymer. Because it is possible to vary the compositional parameters of the cross-linked network copolymers of the invention in an almost limitless fashion, some compositions are both water swellable and oil swellable while others are only water swellable or oil swellable, and some compositions will not be swellable with any of the solvents discussed herein. The amount of crosslinking present in the crosslinked network may be characterized with respect to the degree of swelling exhibited by the network in the fluid. In another embodiment, the crosslinked structure of the network is effective to allow the network to be swollen from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component from the silicone composition of the present invention to leave the original volume, that is, the volume of the polyether siloxane copolymer network in the absence of the fluid.

The compositions of the present invention are self-emulsifying.

The silicone composition may be further processed under low to high shear to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus. Optionally, one or more fluids may be added to the silicone composition prior to the shearing.

In a preferred embodiment, the silicone composition of the present invention is a solid, typically having a creamy consistency, wherein the copolymer network acts as a means for gelling the fluid to reversibly impart characteristics of a solid to the fluid. At rest, the silicone composition exhibits the properties of a solid gel material. The silicone composition of the present invention exhibits high stability and resistance to syneresis, that is, the composition exhibits little or no tendency for fluid to flow from the composition and imparts high stability and syneresis resistance to personal care compositions which include the silicone composition as a component. The high stability and syneresis resistance persists with prolonged aging of such silicone compositions and personal care compositions. However, fluid may be released from the network by subjecting the silicone composition to a shearing force, such as, for example, by rubbing the composition between one's fingers, to provide improved sensory feel characteristic of the fluid component of the silicone material.

Water (or a water equivalent such as a non-aqueous hydroxylic solvent), siloxane, linear or cyclic, or lipophilic fluid (oil swelling agent, oil swellable) may be used as the swelling agent. Lipophilic fluids suitable for use as the fluid component of the composition of the present invention are those compounds or mixtures of two or more compounds that are in the liquid state at or near room temperature, for example, from about 20° C. about 50° C., and about one atmosphere pressure, and include, for example, silicone fluids, hydrocarbon fluids, esters, alcohols, fatty alcohols, glycols and organic oils. In a preferred embodiment, the fluid component of the composition of the present invention exhibits a viscosity of below about 1,000 cSt, preferably below about 500 cSt, more preferably below about 250 cSt, and most preferably below 100 cSt, at 25° C.

In one preferred embodiment, the polyacrylate siloxane copolymer network is a crosslinked network that is insoluble in various fluid components, but that is capable of being swollen by the fluid. The amount of crosslinking present in the crosslinked network may be characterized with respect to the degree of swelling exhibited by the network in the fluid. In another preferred embodiment, the crosslinked structure of the network is effective to allow the network to be swollen by water, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid components from the silicone composition of the present invention to leave the original volume, that is, the volume of the polyacrylate siloxane copolymer network in the absence of the fluid. In another preferred embodiment, the crosslinked structure of the network is effective to allow the network to be swollen by a lipophilic fluid, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid components from the silicone composition of the present invention to leave the original volume, that is, the volume of the polyacrylate siloxane copolymer network in the absence of the fluid. In another preferred embodiment, the crosslinked structure of the network is effective to allow the network to be swollen by a low molecular weight silicone fluid, such as, for example, decamethylcyclopentasiloxane, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component from the silicone composition of the present invention to leave the original volume, that is, the volume of the polyacrylate siloxane copolymer network in the absence of the fluid.

In one embodiment, the fluid component of the present invention comprises an emollient compound. Suitable emollient compound include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and oleyl oleate, as well as fatty acids and alcohols, such as for example, oleyl alcohol and isomyristyl alcohol.

In one embodiment, the fluid component of the present invention comprises a silicone fluid, more preferably a silicone fluid that exhibits emollient properties, preferably a low molecular weight silicone fluid or alternatively a low molecular weight siloxane compound. Suitable silicone fluids include, for example, cyclic silicones of the formula $D_r$, wherein D, $R^8$ and $R^9$ are as previously defined, preferably with $R^8$ and $R^9$ chosen from the group consisting of monovalent one to six carbon atom monovalent hydrocarbon radicals, more preferably methyl, and r is an integer wherein $3 \leq r \leq 12$, such as, for example, hexamethylcyclotrisiloxane ("$D_3$"), octamethylcyclotetrasiloxane ("$D_4$"), decamethylcyclopentasiloxane ("$D_5$"), and dodecamethylcyclohexasiloxane ("$D_6$") as well as linear or branched organopolysiloxanes having the formula:

wherein:

M' is $R^{19}_3SiO_{1/2}$;

D' is $R^{20}_2SiO_{2/2}$;

T' is $R^{21}SiO_{3/2}$ $R^{19}$, $R^{20}$ and $R^{21}$ are each independently alkyl, aryl or aralkyl containing from one to sixty carbon atoms;

u and v are each independently integers from 0 to 300, preferably from 0 to 100, more preferably from 0 to 50, and most preferably from 0 to 20.

In a preferred embodiment, the silicone composition of the present invention comprises, per 100 parts by weight ("pbw") of the silicone composition, from 0.1 to 99 pbw, more preferably from 0.5 pbw to 30 pbw and still more preferably from 1 to 15 pbw of the polyacrylate siloxane copolymer network and from 1 pbw to 99.9 pbw, more preferably from 70 pbw to 99.5 pbw, and still more preferably from 85 pbw to 99 pbw of the fluid.

The polyacrylate siloxane copolymer network compositions of the present invention may be utilized as prepared or as the silicone component in emulsions. As is generally known, emulsions comprise at least two immiscible phases one of which is continuous and the other which is discontinuous. Further emulsions may be liquids with varying viscosities or solids. Additionally the particle size of the emulsions may be render them microemulsions and when sufficiently small microemulsions may be transparent. Further it is also possible to prepare emulsions of emulsions and these are generally known as multiple emulsions. These emulsions may be:

1) aqueous emulsions where the discontinuous phase comprises water and the continuous phase comprises the polyacrylate siloxane copolymer network of the present invention;
2) aqueous emulsions where the discontinuous phase comprises the polyacrylate siloxane copolymer network of the present invention and the continuous phase comprises water;
3) non-aqueous emulsions where the discontinuous phase comprises a non-aqueous hydroxylic solvent and the continuous phase comprises the polyacrylate siloxane copolymer network of the present invention; and
4) non-aqueous emulsions where the continuous phase comprises a non-aqueous hydroxylic organic solvent and the discontinuous phase comprises the polyacrylate siloxane copolymer network of the present invention.

Non-aqueous emulsions comprising a silicone phase are described in U.S. Pat. No. 6,060,546 and co-pending application U.S. Ser. No. 09/033,788 filed Mar. 3, 1998 the disclosures of which are herewith and hereby specifically incorporated by reference.

As used herein the term "non-aqueous hydroxylic organic compound" or "non-aqueous hydroxylic solvent" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a high viscosity cream with good feel characteristics, and high absorbance of volatile siloxanes. It is capable of being blended into formulations for hair care, skin care, antiperspirants, sunscreens, cosmetics, color cosmetics, insect repellants, vitamin and hormone carriers, fragrance carriers and the like.

The personal care applications where the polyacrylate siloxane copolymer network of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the polyacrylate siloxane copolymer network, preferably in the form of the silicone composition of the present invention. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the polyacrylate siloxane copolymer network of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the polyacrylate siloxane copolymer network, preferably in the form of silicone composition of the present invention, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the polyacrylate siloxane copolymer network, preferably in the form of silicone composition of the present invention, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance releasing silicon containing compounds as disclosed in U.S. Pat. Nos. 6,046,156; 6,054,547; 6,075,111; 6,077,923; 6,083,901; and 6,153,578; all of which are herein and herewith specifically incorporated by reference.

The uses of the compositions of the present invention are not restricted to personal care compositions, other products such as waxes, polishes and textiles treated with the compositions of the present invention are also contemplated.

The compositions of the present invention are particularly useful in personal care applications. Using the compositions of the present invention to formulate personal care applications may involve adding materials that are soluble in various solvents or that are insoluble. Subject to routine considerations of chemical reactivity, the components hereinbefore listed may be added at any time before, during or after the synthesis or preparation of the compositions of the present invention provided there is no deleterious effect on the resulting composition. Thus the preparative reactions may be conducted in the presence of solvent systems comprising solutes that are ingredients in cosmetic compositions and likewise the preparative reactions may be conducted in the presence of pigments or other particulate matter resulting in a copolymer matrix polymerized around the pigment or particulate matter encapsulating it.

EXAMPLES

Unless otherwise specified, $R^1$, $R^2$, $R^3$, $R^4$, $R^5$, $R^6$, $R^7$, $R^8$ and $R^{19}$ have been chosen to be methyl in the examples that follow. In U.S. Pat. Nos. 6,531,540 and 6,538,061, herein specifically incorporated by reference in their entirety, R substituents on alkyl substituted D structural units corresponding herein to $R^6$ and $R^7$ have utilized choices for the R groups varying from C1 (methyl) through C16-18 to C30+(C30 to C45).

Example 1

Preparation of Polyacrylate Siloxane Copolymer Network Composition I in Water 234.9 g of an organopolysiloxane with the approximate composition $MD_{85}D^*_{2.2}D''_{5.5}M$ (D*: from the reaction of Si—H with 4-vinylcyclohexene-1,2-epoxide; D'': from the hydrosilylation of Si—H with allyl terminated polyether, $CH_2=CH-CH_2-O-(EO)_{24}(PO)_{27}-CH_3$) and 29.5 g of acrylic acid were mixed. Approximately 20 mg of 4-methoxy phenol and 0.8 g of tetraisopropyl titanate were added. The mixture was heated to 90° C. for approximately 2 hours. Then 72 g of the resulting materials was mixed with 13.36 g of acrylic acid and 341 g of D. I. water. Nitrogen was bubbled through for 30 minutes to remove oxygen from the system. Then 0.86 g of ascorbic acid and 2.58 g of hydrogen peroxide were added. The mixture was stirred for approximately 2 hours to give an opaque soft solid.

Example 2

Preparation of Polyacrylate Siloxane Copolymer Network Composition II in Silicone Fluid 400 g of a silicone hydride fluid with the approximate composition $MD_{125}D^H_{7.5}M$ was mixed with 12.15 g of 4-vinylcyclohexene-1,2-epoxide and 746.55 g of allyl terminated polyether with the formula of $CH_2=CH-CH_2-O-(EO)_{24}(PO)_{27}-CH_3$. The reaction was buffered with sodium propionate. The mixture was heated to 85° C. and 0.7 ml of platinum catalyst solution (10 mg/ml chloroplatinic acid in Ethanol) was added. The mixture was stirred at 90° C. for 3 hours to form an epoxy functional polyether-polysiloxane copolymer. The resulting copolymer was neutralized using sodium bicarbonate, vacuum stripped and filtered. Then 52.31 g of the resulting epoxy functional polyether-polysiloxane copolymer and 1.24 g of acrylic acid were mixed. Approximately 10 mg of 4-methoxy phenol and 0.1 g of tetraisopropyl titanate were added. The mixture was heated to 90° C. for approximately 2 hours. The mixture was then cooled to room temperature and 53.5 g of cyclopentasiloxane was added. Nitrogen was bubbled through for 30 minutes. The mixture was then stirred and heated to 95° C. Then 0.03 g of benzoyl peroxide was added. The mixture was stirred for approximately 2 hours at 95° to give a transparent soft solid.

Example 3

Preparation of Polyacrylate Siloxane Copolymer Network Composition III in Silicone Fluid 200 g of a silicone hydride fluid with the approximate composition $MD_{200}D^H_{7.5}M$ was mixed with 5.99 g of 4-vinylcyclohexene-1,2-epoxide and 84.34 g of allyl terminated polyether with the formula of $CH_2=CH-CH_2-O-(EO)_5(PO)_5-CH_3$. The reaction was buffered with sodium propionate. The mixture was heated to 85° C. and 0.1 ml of platinum catalyst solution (10 mg/ml chloroplatinic acid in Ethanol) was added. The mixture was stirred at 80° C. for 3 hours to form an epoxy functional polyether-polysiloxane copolymer. The resulting copolymer was neutralized using sodium bicarbonate, vacuum stripped and filtered. Then 50.00 g of the resulting epoxy functional polyether-polysiloxane copolymer and 1.59 g of acrylic acid were mixed. Approximately 10 mg of 4-methoxy phenol and 0.1 g of tetraisopropyl titanate were added. The mixture was heated to 90° C. for approximately 2 hours. The mixture was then cooled to room temperature and then 4.66 of acrylic acid and 127.54 g of cyclopentasiloxane were added. Nitrogen was bubbled through for 30 minutes. The mixture was stirred and heated to 100° C. Then 0.07 g of benzoyl peroxide was added. The mixture was stirred for approximately 2 hours at 100° to give a translucent soft solid.

Example 4

Preparation of Polyacrylate Siloxane Copolymer Network Composition IV in Silicone Fluid 870 g of a silicone hydride fluid with the approximate composition $MD_{125}D^H_{7.5}M$ was mixed with 26.06 g of 4-vinylcyclohexene-1,2-epoxide and 366.88 g of allyl terminated polyether with the formula of $CH_2=CH-CH_2-O-(EO)_5(PO)_5-CH_3$. The reaction was buffered with sodium propionate. The mixture was heated to 85° C. and 0.4 ml of platinum catalyst solution (10 mg/ml chloroplatinic acid in Ethanol) was added. The mixture was stirred at 80° C. for 3 hours to form an epoxy functional polyether-polysiloxane copolymer. The resulting copolymer was neutralized using sodium bicarbonate, vacuum stripped and filtered. Then 300.00 g of the resulting epoxy functional polyether-polysiloxane copolymer and 13.07 g of acrylic acid were mixed. Approximately 16 mg of 4-methoxy phenol and 0.47 g of tetraisopropyl titanate were added. The mixture was heated to 90° C. for approximately 2 hours. Then 19.50 g of the resulting materials was mixed with 110.50 g of cyclopentasiloxane. Nitrogen was bubbled through for 30 minutes. The mixture was stirred and heated to 100° C. Then 0.06 g of benzoyl peroxide was added. The mixture was stirred for approximately 2 hours at 100° to give a transparent soft solid.

Example 5

Preparation of Silicone Gel V 10 g of polyacrylate siloxane copolymer network composition I prepared according to Example 1 was mixed with 10 g of water, neutralized to pH 6.5 and homogenized using PowerGen 700D mixer at 7500 RPM for 2 minutes. The resulting Silicone Gel V had a viscosity of 550,000 centiPoise ("cPs") (measured after 24 hours).

Example 6

Preparation of Silicone Gel VI 10 g of polyacrylate siloxane copolymer network composition II prepared according to Example 2 was mixed with 6.7 g of cylcopentasiloxane and homogenized using PowerGen 700D mixer at 7500 RPM for 2 minutes. The resulting Silicone Gel VI had a viscosity of 72,000 cPs (measured after 24 hours).

Example 7

Preparation of Silicone Gel VII 10 g of polyacrylate siloxane copolymer network composition III prepared according to Example 3 was mixed with 10 g of cylcopentasiloxane and homogenized using PowerGen 700D mixer at 7500 RPM for 2 minutes. The resulting Silicone Gel VII had a viscosity of 59,500 cPs (measured after 24 hours).

Example 8

Use of Silicone Gel V as an Aqueous Phase Thickener

The thickened aqueous compositions of Example 8 were made by combining the listed ingredients in the relative amounts set forth below in Table I, according the following procedures. Silicone gel V prepared according to Example 5 was homogenized with D.I. water using PowerGen 700D mixer at 7500 RPM for 2 minute. The viscosities of the resulting materials (measured after 24 hours) are listed in Table I.

TABLE I

| Thickened aqueous compositions | | | |
|---|---|---|---|
| Ingredients | Sample 8-1 | Sample 8-2 | Sample 8-3 |
| Silicone Gel V | 16.7 | 33.3 | 66.7 |
| D.I. water | 83.3 | 66.7 | 33.3 |
| Viscosity (cPs) | 31,500 | 192,500 | 508,500 |

Silicone Gel V provided effective thickening of the aqueous solution.

Example 9

Use of Silicone Gel V as an o/w Emulsifier

Silicone Gel V, prepared according to Example 5 was combined with water, cylcopentasiloxane, bernyl ester and glycerin and mixed until uniform. The stabilities of these emulsions were visually evaluated for obvious phase separation in heating and freeze-thaw tests. In a heating test, the emulsion samples were kept at 50° C. in an oven for 5 days. Three freeze-thaw cycles were done in each freeze thaw test. The compositions and the results of testing completed on these emulsions are summarized in Table II.

TABLE II

| Oil-in-water emulsion compositions | | | | | | |
|---|---|---|---|---|---|---|
| | Ingredients (parts) | | | | Results | |
| Sample | Silicone Gel V | Water | Glycerin | Cylcopenta-siloxane | Bernyl ester | Heating | Freeze-thaw |
| 9-1 | 0.83 | 4.17 | 1.5 | 1.0 | 0.0 | stable | stable |
| 9-2 | 0.83 | 4.17 | 1.5 | 1.0 | 0.0 | stable | stable |
| 9-3 | 0.83 | 4.17 | 1.5 | 0.0 | 1.0 | stable | stable |

The oil-in-water emulsions in Table II showed excellent stability under heating and freeze-thaw conditions.

Example 10

Use of Silicone Gel V in a Liquid Foundation Composition

A liquid foundation composition (Sample 10) and Comparative Example 1 were made by combining the listed ingredients in Table III according to the following procedure: (1) Part A was made by mixing the ingredients until uniform; (2) Part B was then added to part A and mixed until uniform; (3) the mixture was then combined with part C and Part D; (4) the batch was heated to 80° C. and mixed until uniform.

TABLE III

Liquid foundation compositions

| Ingredients | Comparative Example 1 | Sample 10 |
| --- | --- | --- |
| Part A | | |
| Hydroxyethyl cellulose | 0.40 | — |
| Veegum | 0.40 | — |
| Silicone Gel V | — | 5.98 |
| Water | q.s. | q.s. |
| Part B | | |
| Talc | 3.00 | 3.00 |
| Part C | | |
| Cetereth-20 | 5.00 | 5.00 |
| Propylene glycol | 5.00 | 5.00 |
| Glyceryl stearate | 3.00 | 3.00 |
| Isopropyl palmitate | 5.00 | 5.00 |
| Cetyl alcohol | 4.00 | 4.00 |
| Isostearic acid | 4.00 | 4.00 |
| Part D | | |
| Titanium dioxide | 6.00 | 6.00 |
| Iron oxide | 0.94 | 0.94 |

Sensory panel test results showed that Silicone Gel V improved ease of application and after feel of the foundation, including non-tacky, dry and silky feel, compared with the Comparative Example 1.

Example 11

Preparation of Oil-in-Water Emulsion VIII

Silicone Gel V prepared according to Example 5 was combined with water and cyclopentasiloxane and mixed until uniform. The stability of this emulsion was evaluated visually for obvious phase separation. The composition of the emulsion is shown in Table IV.

TABLE IV

Oil-in-water emulsion composition VIII

| Ingredients | Relative amount |
| --- | --- |
| Silicone gel V | 20 |
| Water | 40 |
| Cylcopentasiloxane | 40 |

The oil-in-water Emulsion VIII was stable

Example 12

Use of Oil-in-Water Emulsion VIII in a Skin Treatment Composition

The skin treatment compositions of Sample 12 and Comparative Example 2 were made by combining the ingredients listed in Table V, according to the following procedure: (1) Part B was made by combining all the ingredients and mixing until uniform, (2) Part A and Part B were then combined and mixed until uniform. Oil-in-water Emulsion VIII was made according to Example 11. The sensory properties of the skin treatment composition were evaluated by a sensory panel.

TABLE V

Skin treatment compositions

| | Relative Amount | |
| --- | --- | --- |
| Ingredient | Comparative Example 2 | Sample 12 |
| Part A | | |
| Emulsion VIII | — | 50 |
| Part B | | |
| Hyaluronic acid | 1 | 1 |
| Water | q.s. | q.s. |

Sensory panel tests showed that the oil-in-water emulsion VIII reduced the tacky after-feel of a skin treatment composition, and conferred a cooling feel to the skin treatment composition.

Example 13

Use of Silicone Gel V in a Rinse-Off Hair Conditioner Composition

The rinse-off hair conditioner compositions of Sample 13 and Comparative Example 3 were made by combining the ingredients listed in Table VI, according to the following procedure: (1) Part A was made by combining the ingredients and mixing at 60° C. until uniform; (2) Part B was mixed in a separate container and then added to Part A; (3) the mixture was then mixed until uniform.

TABLE VI

Rinse-off hair conditioner composition

| | Relative Amount | |
| --- | --- | --- |
| Ingredient | Comparative Example 3 | Sample 13 |
| Part A | | |
| Silicone Gel V | — | 19.1 |
| D.I. water | 85 | 65.9 |
| SF1632 | 5 | 5 |
| Tergitol TMN-6 | 0.1 | 0.1 |
| Part B | | |
| Polyquaternium-10 | 1 | 1 |
| Water | q.s. | q.s. |

Panel tests showed that Silicone Gel V improved the softness of the hair and reduced static fly away.

Tergitol TMN-6 Branched Secondary Alcohol Ethoxylates, available at Dow Chemicals SF1632 C16-18 alkyl dimethicone, available at Momentive Performance Materials Inc.
Polyquatemium-10 UCARE polymer JR30M, available at Dow Chemicals

Example 14

Use of Silicone Gel V in a Sunscreen Lotion Composition

The sunscreen lotion composition of Sample 14 was made by combining the ingredients listed in Table VII, according to the following procedure: (1) Part A was made by combining the ingredients and mixing until uniform; (2) Part B was mixed in a separate container and then added to Part A; (3) the mixture was then mixed until uniform.

TABLE VII

| Sunscreen lotion composition | |
|---|---|
| Ingredient | Relative Amount Sample 14 |
| Part A | |
| Silicone Gel V | 13.8 |
| D.I. water | q.s. |
| Glycerin | 5 |
| Part B | |
| Octyl methoxycinnamate | 2 |
| Octyl salicylate | 1 |
| $C_{12-15}$ Alkyl Benzoate | 20 |

A stable o/w sunscreen lotion was prepared. This composition exhibited highly desirable sensory performance during and after rub-in. It also provided an outstanding cooling effect when applied to skin.

Example 15

Use of Silicone Gel VI in a Liquid Lip Color Composition

The liquid lip color compositions of Sample 15 and Comparative Example 4 were made by combining the ingredients listed in Table VIII, according to the following procedure: Silicone Gel VI made according to Example 6 was combined with other ingredients and mixed at 80° C. until uniform. Gloss was evaluated both visually and by using a gloss meter after applying the liquid color formulations onto skin. Long-wear properties of these samples were evaluated by measuring color transfer of the formulation applied to vitro skin. A color meter was used for quantification of the benefit.

TABLE VIII

| Liquid lip color compositions | | |
|---|---|---|
| Ingredients* | Comparative Example 4 | Sample 15 |
| Silicone Gel VI | — | 10 |
| SE 30 | 10 | 10 |
| SF1642 | 2 | 2 |
| SF1528 | 2.6 | 2.6 |
| Isododecane | q.s. | q.s. |
| Red pigment | 29 | 29 |
| TiO2 | 2.9 | 2.9 |

Both visual and gloss meter measurement results showed that Silicone Gel VI improved the gloss of the liquid lip color formula. Color meter tests showed Silicone Gel VI also improved color intensity and reduced color transfer.

SE30 Polydimethylsiloxane gum, available at Momentive Performance Materials Inc.
SF1642 C30-45 alkyl dimethicone, available at Momentive Performance Materials Inc.
SF1528 Cyclopentasiloxane (and) PEG/PPG-20/15 dimethicone, available at Momentive Performance Materials Inc.
Red pigment Red 7 lake dispersion, Kobo C020R7C (castor oil, Red 7 Lake and isopropyl titanium triisostearate), available at Kobo

Example 16

Use of Polyacrylate Siloxane Copolymer Network Composition III as a w/o Emulsifier Silicone Network Composition III prepared according to Example 3 was combined with water, cyclopentasiloxane and glycerin and mixed until uniform. The stabilities of these emulsions were visually evaluated for obvious phase separation in heating and freeze-thaw tests. The compositions of these emulsions are shown in Table IX.

TABLE IX

| Water-in-oil emulsion compositions | | |
|---|---|---|
| Ingredients | Comparative Example 5 | Sample 16 |
| polyacrylate siloxane copolymer network composition III | 0 | 20 |
| cyclopentasiloxane | 60 | 40 |
| Glycerin | 8 | 8 |
| Water | 32 | 32 |

The w/o emulsion of Sample 16 showed excellent stability under heating (to 50° C.) and freeze-thaw conditions. A w/o emulsion could not be made by mixing the ingredients of Comparative Example 5.

Example 17

Use of Silicone Gel VII in a Moisturizer Composition

The moisturizer compositions of Sample 17 and Comparative Example 6 were made by combining the ingredients listed in Table X, according to the following procedure: (1) Part A was made by combining the ingredients and mixing until uniform at 60° C.; (2) Part B was added to Part A and mixed until uniform; (3) Part C was mixed in a separate container and then added to the mixture of Part A and Part B; (4) the mixture was mixed at 60° C. until uniform. The stabilities of these compositions were visually evaluated for obvious phase separation in heating and freeze-thaw tests. Sensory properties were evaluated by an expert panel.

TABLE X

Moisturizer compositions

| Ingredient* | Relative Amount | |
|---|---|---|
| | Comparative Example 6 | Sample 17 |
| Part A | | |
| Silicone Gel VII | — | 25 |
| SF1540 | 2.5 | 2.5 |
| D5 | 37.5 | 12.5 |
| SF1550 | 5 | 5 |
| SF96-1000 | 5 | 5 |
| Part B | | |
| SF1632 | 2 | 2 |
| Tospearl 2000B | 5 | 5 |
| Part C | | |
| Tween 20 | 0.2 | 0.2 |
| Sodium chloride | 1 | 1 |
| Water | q.s. | q.s. |

The moisturizer composition of Sample 17 showed excellent stability under heating (to 50° C.) and freeze-thaw conditions. The control sample showed obvious phase separation in the heating condition. Sensory panel test results showed that Silicone Gel VII improved substantivity, cooling effect on skin and after-feel of the moisturizer composition, compared with Comparative Example 6.

*SF1540 Cyclopentasiloxane (and) PEG/PPG-20/15 Dimethicone, available at Momentive Performance Materials Inc.

SF1550 Phenyl Trimethicone, available at Momentive Performance Materials Inc.

SF96-1000 Polydimethylsiloxane fluid, available at Momentive Performance Materials Inc.

SF1632 Cetearyl Methicone, available at Momentive Performance Materials Inc.

Tospearl 2000B Polymethylsilsesquioxane, Available at Momentive Performance Materials Inc.

Tween 20 Polyoxyethylene(20) sorbitan monolaurate, Available at GE Healthcare

Example 18

Use of Silicone Gel VII in a Leave-on Hair Conditioner Composition

The leave-on hair conditioner compositions of Sample 18 and Comparative Example 7 were made by combining the ingredients listed in Table XI and mixing until uniform.

(Note that the aminofunctional silicone, SF1708, can be blended with Silicone Gel VII prior to making the hair conditioner composition. The blends of SF1708 and Silicone Gel VII exhibited a high viscosity.)

TABLE XI

Leave-on hair conditioner compositions

| Ingredient* | Relative Amount | |
|---|---|---|
| Part A | Comparative Example 7 | Sample 18 |
| Silicone Gel VII | — | 2.5 |
| SF1708 | 1 | 1 |
| Cylcopentasiloxane | q.s. | q.s. |

Panel tests showed the composition of Sample 18, when applied to hair, provided a softer feel compared with Comparative Example 7, and in contrast to Comparative Example 7, provided a non-tacky feel.

*SF1708 Amodimethicone, Available at Momentive Performance Materials Inc.

Example 19

Use of Polyacrylate Siloxane Copolymer Network Composition IV in a Rinse-resistant Water-in-oil Sunscreen Lotion Composition A rinse-resistant water-in-oil sunscreen lotion formulation was made by combining the ingredients listed in table XII, according to the following procedure: (1) Part B was made by combining the ingredients and mixing until uniform; (2) Part A was added to Part B and mixed until uniform; (3) Part C was mixed in a separate container and then added to the mixture of Part A and Part B; (4) the mixture was then mixed until uniform. The stability of this composition was visually evaluated for obvious phase separation in heating and freeze-thaw tests. Sensory properties were evaluated by a sensory panel. Rinse-resistance of this composition was evaluated by in-vitro SPF measurement on vitro skin before and after immersed in stirred water for 40 minutes.

TABLE XII

Rinse-resistant water-in-oil sunscreen lotion composition

| Ingredients | Relative Amount Sample 19 |
|---|---|
| Part A | |
| Silicone Network Composition IV | 15 |
| Part B | |
| Octyl methoxycinnamate | 7.5 |
| Benzophenone-3 | 3 |
| Octyl salicylate | 5 |
| $C_{12-15}$ Alkyl Benzoate | 4.5 |
| Part C | |
| Water | 60 |
| Glycerin | 5 |

The rinse-resistant water-in-oil sunscreen lotion composition of Example 19 showed excellent stability under the heating (to 50° C.) and freeze-thaw conditions. It exhibited a highly desirable sensory feel, a cooling effect on the skin. In-vitro SPF measurement on vitro skin determined before and after immersed in stirred water for 40 minutes were 25 and 25 respectively (average of 3 measurements). polyacrylate siloxane copolymer network composition IV provided about 100% SPF retention following a rinse treatment with water. Furthermore, when the composition was applied to the skin, not only was the film formed on the skin surface repellent to water and resistant to rinsing by water, water was actually capable of being absorbed by the film, or emulsified into the film, thus preserving the integrity of the film on the skin. This is expected to confer some or all of the benefits of water-proofing, rinse-resistance, and tolerance to sweat.

Example 20

Preparation of Polyacrylate Siloxane Copolymer Network Composition IX in Water 434 g of an organopolysiloxane with the approximate composition $MD_{85}D^*_{2.2}D''_{5.5}M$ (D*: from the reaction of Si—H with 4-vinylcyclohexene-1,2-epoxide; D'': from the hydrosilylation of Si—H with allyl terminated polyether, $CH_2=CH-CH_2-O-(EO)_{24}(PO)_{27}-CH_3$) and 54 g of acrylic acid were mixed. Approximately 30 mg of 4-methoxy phenol and 1.0 g of tetraisopropyl titanate were added. The mixture was heated to 90° C. for approximately 2 hours. Then 6 g of the resulting material was mixed with 29 g of Sipomer PAM-200 (Phosphate ester of polypropylene glycol monomethacrylate, available from Rhodia), 1 g of Tergitol TMN-6 and 63.56 g of D. I. water. The mixture was neutralized to pH 6.5. Nitrogen was bubbled through for 30 minutes to remove oxygen from the system. Then 0.14 g of sodium bisulfite and 0.3 g of potassium persulfate were added. The mixture was heated at 50° C. for approximately 17 hours to give an opaque soft solid.

Example 21

Preparation of Polyacrylate Siloxane Copolymer Network Composition X in Water 6 g of Polysiloxane Copolymer A* was mixed with 29 g of Sipomer PAM-200, 1 g of Tergitol TMN-6 and 63.56 g of D. I. water. The mixture was neutralized to pH 6.5. Nitrogen was bubbled through for 30 minutes to remove oxygen from the system. Then 0.14 g of sodium bisulfite and 0.3 g of potassium persulfate were added. The mixture was heated at 50° C. for approximately 17 hours to give an opaque soft solid.
*Polysiloxane Copolymer A: Acrylated siloxane polyalkyleneoxide copolymer. $CH_2=CH-CO(OC_2H_4)_8OC_3H_6Si(CH_3)_2(-OSi(CH_3)_2)_{15}OSi(CH_3)_2C_3H_6O(C_2H_4)_8COCH=CH_2$
Available at Momentive Performance Materials Inc.

Example 22

Use of Functionalized Silicone Network IX as an Aqueous Phase Thickener

The thickened aqueous composition of Example 22 was made by combining the listed ingredients in the relative amounts set forth below in Table XIII, according the following procedures. Functionalized Silicone Network IX prepared according to Example 20 was homogenized with D.I. water using PowerGen 700D mixer at 7500 RPM for 2 minutes. pH was adjusted by using citric acid.

TABLE XIII

Thickened aqueous composition

| Ingredients | Sample 22 |
| --- | --- |
| Functionalized Silicone Network IX | 16.7 |
| D.I. water | 83.3 |
| Viscosity at pH 3.5 (cPs) | 16,500 |

TABLE XIII-continued

Thickened aqueous composition

| Ingredients | Sample 22 |
| --- | --- |
| Viscosity at pH 5.5 (cPs) | 46,000 |
| Viscosity at pH 7 (cPs) | 69,000 |

Polyacrylate siloxane copolymer network composition IX provided effective thickening of the aqueous solution in the range of pH 3.5-7.

Example 23

Use of Polyacrylate Siloxane Copolymer Network Composition X as an Aqueous Phase Thickener The thickened aqueous composition of Example 23 was made by combining the listed ingredients in the relative amounts set forth below in Table XIV, according the following procedures. Functionalized Silicone Network X prepared according to Example 21 was homogenized with D.I. water using PowerGen 700D mixer at 7500 RPM for 2 minutes. pH was adjusted by using citric acid.

TABLE XIV

Thickened aqueous composition

| Ingredients | Sample 23 |
| --- | --- |
| Functionalized Silicone Network X | 16.7 |
| D.I. water | 83.3 |
| Viscosity at pH 4 (cPs) | 7,000 |
| Viscosity at pH 5.5 (cPs) | 14,000 |
| Viscosity at pH 7 (cPs) | 33,000 |

Functionalized Silicone Network X provided effective thickening of the aqueous solution in the range of pH 4-7.

Example 24

Use of Polyacrylate Siloxane Copolymer Network Composition IX in an Alpha Hydroxy Acid Skin-treatment Cream Composition An alpha hydroxy acid skin-treatment cream composition (Sample 24) and Comparative Example 8 and 9 were made by combining the listed ingredients in Table XV according to the following procedure: (1) Part A was made by mixing the ingredients until uniform; (2) Part B was then added and mixed until uniform; (3) the mixture was heated to 50° C. and Part C was added; (4) The mixture was then heated to 75° C.; (5) All the ingredients in Part D were mixed in a separate container at 75° C. and then added to the mixture of Part A, B and C; (6) The batch was mixed at 75° C. until uniform; (7) the mixture was then cooled to 40° C.; (8) The ingredients of Part E were then added in the order shown; (9) The batch was stirred until uniform and cooled to room temperature.

TABLE XV

Alpha hydroxy acid skin-treatment cream composition

| Ingredients | Comparative Example 8 | Comparative Example 9 | Sample 24 |
|---|---|---|---|
| Part A | | | |
| Hydroxyethyl cellulose | — | 0.29 | — |
| Veegum | — | 1.43 | — |
| Functionalized silicone network composition IX | — | — | 6.00 |
| Water | q.s. | q.s. | q.s. |
| Part B | | | |
| Glycerin | 4.76 | 4.76 | 4.76 |
| Part C | | | |
| Triethanolamine | 0.71 | 0.71 | 0.71 |
| Part D | | | |
| Cetyl alcohol | 2.85 | 2.85 | 2.85 |
| Glyceryl stearate (and) PEG-100 stearate (Arlacel 165) | 4.28 | 4.28 | 4.28 |
| Stearic acid | 1.43 | 1.43 | 1.43 |
| Isopropyl myristrate | 4.28 | 4.28 | 4.28 |
| Mineral oil | 4.28 | 4.28 | 4.28 |
| Dimethicone, 500 cst | 1.43 | 1.43 | 1.43 |
| Part E | | | |
| Glycolic acid (70%) | 7.14 | 7.14 | 7.14 |
| Sodium hydroxide | 2.66 | 2.66 | 2.66 |

Sensory panel test results showed that polyacrylate siloxane copolymer network composition IX improved ease of application and after feel of the alpha hydroxy acid skin-treatment cream, including non-tacky, dry and silky feel, compared with the Comparative Example 9. The results also showed that polyacrylate siloxane copolymer network composition IX improved ease of application and increased viscosity and substantivity of the skin-treatment cream composition, compared with the Comparative Example 8.

Example 25

Preparation of Polyacrylate Siloxane Copolymer Network Composition XI in Silicone Fluid 900 g of a silicone hydride fluid with the approximate composition $MD_{125}D^{H}_{7.7}M$ was mixed with 29.93 g of 4-vinylcyclohexene-1,2-epoxide and 386.28 g of allyl terminated polyether with the formula of $CH_2=CH-CH_2-O-(EO)_5(PO)_5-CH_3$. The reaction was buffered with sodium propionate. The mixture was heated to 85° C. and 0.67 ml of platinum catalyst solution (10 mg/ml chloroplatinic acid in Ethanol) was added. The mixture was stirred at 85° C. for 1 hour to form an epoxy functional polyether-polysiloxane copolymer. The resulting copolymer was neutralized using sodium bicarbonate, vacuum stripped and filtered. Then 300.00 g of the resulting epoxy functional polyether-polysiloxane copolymer and 13.5 g of acrylic acid were mixed. Approximately 6 mg of 2,2,6,6-Tetramethylpiperidine 1-oxyl and 1.05 g of tetraisopropyl titanate were added. The mixture was heated to 90° C. for approximately 3 hours. Then 150.00 g of the resulting materials was mixed with 350.00 g of cyclopentasiloxane. Nitrogen was bubbled through for 30 minutes. The mixture was stirred and heated to 100° C. Then 0.31 g of dilauroyl peroxide was added. The mixture was stirred for approximately 2 hours at 100° to give a translucent soft solid.

Example 26

Preparation of Silicone Gel XII 100 g of polyacrylate siloxane copolymer network composition XI prepared according to Example 25 was mixed with 100 g of cylcopentasiloxane and mixed using an overhead mixer at 600 RPM for 30 minutes. The resulting Silicone Gel XII had a viscosity of 94,000 centipoise ("cPs") (measured after 24 hours).

Example 27

Use of Silicone Gel XII in an Oil-in-Water Skin Lightening Lotion Composition

The skin lightening lotion composition of Sample 27 was made by combining the ingredients listed in Table XVI, according to the following procedure: (1) The oil phase ingredients except cyclopentasiloxane were combined, heated to 75° C. and mixed at 500 RPM until uniform; (2) The water phase ingredients except triethanolamine and Germaben-IIE were combined, heated to 75° C. and mixed at 500 RPM until uniform; (3) The oil phase mixture was then added slowly to the water phase mixture at 75° C.; (4) The mixture was cooled to 40° C. and mixed at 400 RPM until uniform; (5) Cylopentasiloxane, triethanolamine and Germaben-IIE were then added into the mixture; (6) The mixture was stirred at 400 RPM until uniform and cooled to room temperature.

TABLE XVI

Oil-in-water skin lightening lotion composition

| Ingredients | Weight percent Sample 27 |
|---|---|
| Oil Phase | |
| Steareth-2 | 2 |
| Steareth-21 | 1.5 |
| Cyclopentasiloxane | 3 |
| Silicone Gel XII | 5 |
| Carylyl Methicone | 3 |
| Trimethylsiloxysilicate (and) cyclopentasiloxane | 0.5 |
| Tocopherol acetate | 0.3 |
| PF-5 TiO2 CR50 | 0.3 |
| C12-15 Alkylbenzoate | 0.6 |
| Benzophenone-3 | 2 |
| Octylmethoxycinnamate | 4 |
| Butylmethoxydibenzyolmethane | 1.5 |
| Water Phase | |
| DI Water | 67.79 |
| Glycerin | 5 |
| Niacinamide | 2 |
| Panthenol | 1 |
| Tetrasodium EDTA | 0.08 |
| Carbomer 941 | 0.16 |
| Germaben - IIE | 0.07 |
| Triethanolamine | 0.16 |
| Sodium ascorbyl phosphate | 0.04 |

This illustrative example demonstrates that Silicone Gel XII can easily be formulated into oil-in-water emulsions. Sensory panel test results showed that this skin lightening lotion composition exhibited an especially luxurious silky feel with slip and cushioning.

Example 28

Use of Silicone Gel XII in a Sprayable Composition

The sprayable composition of Example 28 was made by mixing all the ingredients listed in Table XVII at room temperature in the order listed in the table.

TABLE XVII

Sprayable composition

| Ingredients | Weight percent Example 28 |
| --- | --- |
| Diisostearyl trimethylolpropanesiloxy silicate | 8 |
| C12-15 Alkylbenzoate | 10 |
| Phenyl trimethicone | 15 |
| Trimethylsiloxysilicate (and) cyclopentasiloxane | 5 |
| Octylmethoxycinnamate | 7 |
| Octocrylene | 8 |
| Silicone Gel XII | 5 |
| Ethyl trisiloxane | 42 |

This example demonstrated that Silicone Gel XII could be easily incorporated in a sprayable composition yielding a luxurious silky feel without problem of thickening or clogging.

Example 29

Use of Silicone Gel XII in an Antiperspirant Gel Composition

The antiperspirant gel composition of Example 29 was made by combining the ingredients listed in Table XVIII, according to the following procedure:
(1) Part A was made by combining the ingredients and mixing at 600 RPM until uniform;
(2) Part B was made by combining the ingredients and mixing at 600 RPM until uniform;
(3) Part B was added dropwise to Part A and mixed at 600 RPM until uniform.

TABLE XVIII

Antiperspirant gel composition

| Ingredients | Weight percent Sample 29 |
| --- | --- |
| Part A | |
| Cyclopentasiloxane (and) PEG/PPG-20/15 Dimethicone | 1.87 |
| Cyclopentasiloxane | 8.13 |
| Hydrogenated polydecene | 3 |
| Silicone Gel XII | 5 |
| Part B | |
| 45% Aluminum zirconium tetrachlorohydrex glycol | 47 |
| Propylene glycol | 21 |
| DI water | 14 |

This illustrative example showed the use of Silicone Gel XII in an antiperspirant application. The antiperspirant gel composition of Sample 29 exhibited a unique pleasant feel. Matching the refractive indices of water and oil phase by varying the propylene glycol to water ratio can yield also clear AP gels.

Example 30

Use of Silicone Gel XII in a Low pH Alpha-hydroxy-Acid (AHA) Cream Composition The low pH alpha-hydroxy-acid cream composition of Example 30 was made by combining all the ingredients listed in Table XIX, according to the following procedure: (1) Part A was made by combining all the ingredients and mixing at 60° C. until uniform; (2) Part B was made by combining all the ingredients and mixing at 60° C. until uniform; (3) Part B was added to Part A dropwise and the mixture was stirred until uniform; (4) Part C was added to the mixture to adjust the composition to pH 4.

TABLE XIX

Low pH alpha-hydroxy-acid cream composition

| Ingredients | Weight percent |
| --- | --- |
| Part A | |
| PEG-8 Dimethicone | 6 |
| Silicone Gel XII | 20 |
| Octylmethoxycinnamate | 7.5 |
| Cyclopentasiloxane (and) PEG/PPG-20/15 Dimethicone | 3 |
| Part B | |
| Glycerin | 12 |
| NaCl | 0.5 |
| 70% Glycolic acid | 4.4 |
| DI Water | 43.20 |
| Part C | |
| Triethanolamine | 3.4 |

This AHA cream composition showed good stability at room temperature. It exhibited a luxurious skin feel, which was very different from the "AHA-sting" feel of most other low pH AHA products.

Example 31

Use of Silicone Gel XII in a Lipstick

The lipstick composition of Sample 31 was made by combining the ingredients listed in Table XX, according to the following procedure: (1) Part A was made by combining all the ingredients and mixing at 98° C. for 15 until uniform; (2) The ingredients in Part B were added to Part A and the mixture was stirred until uniform; (3) The mixture was then poured into a lipstick mold that had been pre-warmed in a 50° C. oven; (4) The mold was then placed in a −10° C. freezer until the mixture solidified; (5) Then mold was removed from the freezer; (6) The solidified mixture was removed from the mold and put into a lipstick case.

TABLE XX

Lipstick composition

| Ingredients | Weight percents Sample 31 |
|---|---|
| Part A | |
| Snow white petrolatum | 25.9 |
| Diisostearoyl Trimethylolpropanesiloxy silicate | 15 |
| Silicone Gel XII | 5 |
| Candelilla wax | 4 |
| White beeswax | 6 |
| Ozokerite | 7 |
| Yellow carnuba wax | 4 |
| Red dye/Castor oil | 28 |
| Part B | |
| Isododecane | 5 |
| Propylparaben | 0.1 |

The lipstick composition of Sample 31 exhibited unique softness and silkiness.

Example 32

Use of Silicone Gel XII in a Liquid Lip Color Composition

The liquid lip color compositions of Sample 32 and Comparative Example 10 were made by combining the ingredients listed in table XXI, according to the following procedure: (1) All the ingredients were put in to a container and heated at 90° C. for 30 minutes; (2) The mixture was then mixed in a Flack-Tec mixer at 3500 RPM for 5 minutes. The liquid lip compositions were applied to vitro skin and subjected to gloss measurement. Gloss was evaluated by using a BYK-Gardner Micro TRI gloss meter. The gloss measurement results are shown in Table XXII.

TABLE XXI

Liquid lip color compositions

| Ingredients | Weight percent Comparative Example 10 | Weight percent Sample 32 |
|---|---|---|
| Dimethicone* | 10 | 10 |
| Cyclopentasiloxane (and) C30-45 Alkyl Cetearyl Dimethicone Crosspolymer | 26.3 | 21.3 |
| Silicone Gel XII | — | 5 |
| C30-45 Alkyl Dimethicone | 2 | 2 |
| Cyclopentasiloxane (and) PEG/PPG 20/15 Dimethicone | 2.6 | 2.6 |
| Isododecane | 27.3 | 27.3 |
| Red Pigment | 29 | 29 |
| TiO2 | 2.9 | 2.9 |

TABLE XXII

Gloss measurement results of Sample 32 and Comparative Example 10

| Composition | Reflectance at angle (°) | Aver. Value | SD |
|---|---|---|---|
| Comparative Example 10 | 20 | 2.5 | 0.0 |
| Comparative Example 10 | 60 | 22.2 | 0.0 |
| Comparative Example 10 | 85 | 47.4 | 0.1 |
| Sample 32 | 20 | 3.3 | 0.0 |
| Sample 32 | 60 | 35.9 | 0.0 |
| Sample 32 | 85 | 54.3 | 0.6 |

The gloss measurement results showed that Silicone Gel XII improved gloss of this lip color composition, compared with Comparative Example 10.

Example 33

Use of Silicone Gel XII in a Rinse-off Bath Conditioner

The rinse-off bath conditioner compositions of Sample 33 and Comparative Example 11 were made by combining the ingredients listed in Table XIII and mixing until uniform.

Approximately 0.02 gram of the formulation was applied on the tester's arm skin in the area of 3 cm×3 cm. The skin was then washed with approximately 0.5 ml of detergent (30% of Standapol ES-1 in water) for 20 sec and rinsed with warm water for 20 seconds. The skin was then dried with a paper tower. The fragrance left on the arm skin was evaluated by a panel of three persons having a normal sense of smell.

TABLE XXIII

Rinse-off bath conditioner compositions

| Ingredient* | Relative Amount | |
|---|---|---|
| Part A | Comparative Example 11 | Sample 33 |
| Silicone Gel XII | — | 15 |
| SF96-350 | 15 | — |
| Starlet | 5 | 5 |

Panel tests showed the Silicone Gel XII improved the fragrance retention of this rinse-off bath conditioner composition of Sample 33, compared with Comparative Example 11.

SF96-350 Polydimethylsiloxane, available at Momentive Performance Materials Inc.

Starlet Fragrance oil, available at Givaudan

Example 34

Use of Silicone Gel XII as an Oil Phase Thickener

The thickened compositions of Example 34 were made by combining the listed ingredients in the relative amounts set forth below in Table XXIII, according to the following procedure: Silicone gel XII prepared according to Example 26 was mixed with cyclopentasiloxane or Finsolv TN using an overhead mixer at 600 RPM for 20 minute. The viscosities of the resulting materials (measured after 24 hours) are listed in Table XXIV.

TABLE XXIV

Thickened oil compositions

| Ingredients | Sample 34-1 | Sample 34-2 | Sample 34-3 |
|---|---|---|---|
| Silicone Gel XII | 20.00 | 20.00 | 20.00 |
| Cylcopentasiloxane | 20.00 | — | 19.00 |
| Finsolv TN | — | 20.00 | — |
| MagnaSoft Plus | — | — | 1.00 |
| Viscosity (cPs) | 2,000 | 3,200 | 29,500 |

Silicone Gel XII provided thickening in Silicone oil and organic oil. The thickening effect in silicone oil was more significant when Silicone Gel XII was combined with amino silicone.

Magnasoft Plus Amino modified silicone fluid, available at Momentive Performance Materials.

Example 35

Use of Silicone Gel XII in a Rinse-Off Hair Conditioner

A rinse-off hair conditioner formulation was made by combining the ingredients listed in table XXV, according to the following procedure: (1) Part B was made by combining the ingredients and mixing until uniform; (2) Part C was then mixed with the ingredients in Part C at 70° C. until uniform; (3) The mixture of Part B and Part C was then added to Part A; (4) The mixture was mixed at 70° C. until uniform and then cooled to 35° C. while being mixed. This rinse-off conditioner formulation was tested on platinum blond hair tresses. Duplicate platinum blond hair tresses were washed under standard laboratory procedures with a model shampoo formulation, followed by treatment with the rinse-off hair conditioner formulation of Sample 35. These tresses were then washed and dried using a blow drier. Dry detangling was measured and is defined as the number of inches a comb travels when the tress is placed on a calibrated chart and is combed from top to bottom. Static control was evaluated by measuring fly-away. Hair was combed quickly for ten times and fly-away is defined as the difference between the total width of the entire tress and the width of the hair bundle after the hair has been combed. Lower fly-away indicates better static control.

TABLE XXV

Rinse-off hair conditioner composition

| Ingredients | Weight percents Sample 35 |
|---|---|
| Part A | |
| D.I. water | 88 |
| Part B | |
| Gel XII | 2 |
| Decapryl ether | 2 |
| Part C | |
| Cetyl alcohol | 2 |
| Ceteareth-20 | 2 |
| Cetearyl alcohol | 4 |

TABLE XXVI

Dry detangling and fly-away measurement results of Sample 35

| | Treatment on the hair tresses | |
|---|---|---|
| | Treated with Sample 35 after shampoo | No treatment after shampoo |
| Dry detangling (inches) | 4.5 | 3.4 |
| Fly away (inches) | 2.8 | 5.0 |

The measurement results in Table XXVI showed that the rinse-off hair conditioner composition of Sample 35 improved dry detangling and provided static control. Panel test also showed that the composition of Sample 35 improved softness of the hair tresses.

Example 36

Use of Silicone Gel XII in a Leave-on Hair Serum

A leave-on hair serum formulation was made by mixing the ingredients listed in table XXVII at room temperature as ordered. This leave-on hair serum formulation was tested on platinum blond hair tresses. Duplicate platinum blond hair tresses were washed under standard laboratory procedures with a model shampoo formulation, followed by treatment with the rinse-off hair conditioner formulation of Sample 36. These tresses were then dried using a blow drier. Dry detangling and fly-away were measured as in Example 35.

TABLE XXVII

Leave-on hair serum composition

| Ingredients | Weight percents Sample 36 |
|---|---|
| Gel XII | 2 |
| SF 1215 | 50 |
| Isododecane | 29.5 |
| Isostearyl alcohol | 12 |
| Isopropyl myristate | 6.5 |

* SF1215 Cylcopentasiloxane and dimethicone, available at Momentive Performance Materials.

TABLE XXVIII

Dry detangling and fly-away measurement results of Sample 36

| | Treatment on the hair tresses | |
|---|---|---|
| | Treated with Sample 35 after shampoo | No treatment after shampoo |
| Dry detangling (inches) | 4.2 | 3.5 |
| Fly away (inches) | 0.0 | 5.0 |

The measurement results in Table XXVIII showed that the leave-on hair serum composition of Sample 36 improved dry detangling and provided static control. Panel test also showed that the composition of Sample 36 improved softness of the hair tresses.

Example 37

Use of Silicone Gel XII in a Hair Styling Composition

A hair styling formulation was made by mixing the ingredients listed in table XXIX. This hair styling formulation was tested on light brown hair tresses. Duplicate hair tresses were wetted followed by treatment with the hair styling formulation of Example 37. These treated hair tresses were rolled around hair rollers, dried in an oven at temperature of 100° c. for one hour and then conditioned at ambient temperature overnight. These hair tresses were then carefully removed from the roller and hung on a ruler rack. The lengths of these hair tresses were measured and recorded as the initial lengths. The tresses on the ruler rack were then put in a 25° C. and 90% Relative Humidity chamber. Length measurements were taken every 15 minutes for 2 hours. Curl retention for each treated hair tress was calculated using the following formula.

$$\text{Curl Retention \%} = \frac{L - L^t}{L - L_o} \times 100$$

Where: L Length of hair fully extended
$L_o$ Length of hair before being put in the humidity chamber
$L^t$ Length of hair t minutes after being put in the humidity chamber

TABLE XXIX

Hair styling compositions

| | Weight percents | | |
|---|---|---|---|
| Ingredients | Comparative Example 12 | Sample 37-1 | Sample 37-2 |
| Silicone Gel XII | — | 50 | 50 |
| Cylcopentasiloxane | 100 | 50 | 49 |
| SF 1708 | — | — | 1 |

TABLE XXX

Curl retention measurement results of Example 37

| | Treatment | | |
|---|---|---|---|
| Time after being put in the humidity chamber (min) | Comparative Example 12 Curl retention % | Sample 37-1 Curl retention % | Sample 37-2 Curl retention % |
| 0 | 100 | 100 | 100 |
| 15 | 33 | 62 | 79 |
| 30 | 25 | 54 | 79 |
| 45 | 17 | 54 | 71 |
| 60 | 17 | 46 | 71 |
| 75 | 17 | 46 | 71 |
| 90 | 17 | 46 | 71 |
| 105 | 17 | 46 | 71 |
| 120 | 17 | 46 | 71 |

The measurement results shown in Table XXX showed that Gel XII enhanced hair curl retention significantly compared with Comparative Example 12. The combination of Gel XII and SF1708, an amino-functional silicone, provided even higher hair retention than Gel XII itself. This is a surprising result since the SF1708 at a level of 1% in cyclopentasiloxane provides no additional curl retention benefit compared to cyclopentasiloxane alone. Thus, Gel composition XII combined with an aminosilicone fluid provides a clear and unexpected synergistic curl retention benefit.

Panel tests showed that the composition of Sample 37-1 or 37-2, when applied to hair, provided a smoother feel, less frizz and better hair alignment compared with Comparative Example 12.

Example 38

Use of Silicone Gel XII as an w/o Emulsifier

Silicone Gel XII, prepared according to Example 26 was combined with the other ingredients listed in Table XXXI, according to the following procedure: (1) Part A was made by mixing the ingredients until uniform; (2) Part B was made in a separate container by mixing the ingredients until uniform. (3) Part B was added slowing to Part A and the mixture was mixed until uniform. The viscosities of these emulsions were measured 24 hours after the emulsions were made. The stabilities of these emulsions were visually evaluated for obvious phase separation in heating and freeze-thaw tests. In a heating test, the emulsion samples were kept at 50° C. in an oven for 5 days. Three freeze-thaw cycles were done in each freeze thaw test. The compositions and the results of testing completed on these emulsions are summarized in Table XXXI.

TABLE XXXI

Water in oil emulsion composition

| | Relative Amount | |
|---|---|---|
| Ingredient | Sample 38-1 | Sample 38-2 |
| Part A | | |
| Silicone Gel XII | 15 | 15 |
| Octyl methoxycinnamate | 1.5 | 1.44 |
| Octyl salicylate | 1.0 | 0.96 |
| $C_{12-15}$ Alkyl Benzoate | 17.5 | 16.85 |
| Magnasoft Plus | — | 0.75 |
| Part B | | |
| D.I. water | 60 | 60 |
| Glycerin | 5 | 5 |
| Results | | |
| Viscosity (cPS) | 19,500 | 63,500 |
| Freeze-thaw test | Pass | Pass |
| Oven test | Pass | Pass |

The water in oil emulsion compositions of Sample 38-1 and 38-2 showed excellent free-thaw and heat stabilities. The viscosity measurement results also showed that the combination of Silicone Gel XII and Magnasoft Plus, an aminofunctional silicone, provided better thickening in water in oil emulsion than Silicone Gel XII itself.

Example 39

Preparation of Silicone Gel XIII 100 g of polyacrylate siloxane copolymer network composition XI prepared according to Example 25 was combined with 98 g of cylcopentasiloxane and 2 g of SF1708 aminofunctional silicone fluid and mixed using an overhead mixer at 600 RPM for 30 minutes to produce Silicone Gel XIII.

Samples of Silicone Gel XII and Silicone Gel XIII were placed on an aluminum surface and the cyclopentasiloxane allowed to evaporate at ambient temperature and humidity. This produced a film. The film that was formed was evaluated after 48 h for tackiness on a scale of 0-10 (where 0 is no tack, and 10 is "Very tacky"). The results of the tack evaluation are given in Table XXXII.

TABLE XXXII

Tack evaluation for films produced from Gel compositions.

|  | Gel XII | Gel XIII |
|---|---|---|
| Tack Feeling | 8 | 2 |

The results of the tack evaluation clearly show that the film produced from Gel XIII has very little tack, and is much less tacky than the film produced from Gel XII.

This is a surprising result since the amino-functional silicone fluid, SF1708, when spread as a thin film, has a high level of tack. Thus, it is surprising that the incorporation of a fluid with a high level of tack into the Gel composition XIII, would have the effect of producing a film that has a very low level of tack.

Example 40

Preparation of Functionalized Silicone Network Composition XIII in Silicone Fluid 1000 g of a silicone hydride fluid with the approximate composition $MD_{125}D^H{}_{7.7}M$ was mixed with 34.18 g of 4-vinylcyclohexene-1,2-epoxide and 470.36 g of allyl terminated polyether with the formula of $CH_2=CH-CH_2-O-(EO)_5(PO)_5-CH_3$. The mixture was heated to 85° C. and 0.40 g of platinum catalyst solution (10 mg/ml chloroplatinic acid in Ethanol) was added. The reaction was buffered with sodium propionate. The mixture was stirred at 85° C. for 2 hours to form an epoxy functional polyether-polysiloxane copolymer. The copolymer was then neutralized with sodium bicarbonate, vacuum stripped and filtrated. Then 150.00 g of the resulting epoxy functional polyether-polysiloxane copolymer and 1.40 g of acrylic acid were mixed. Approximately 3 mg of 2,2,6,6-Tetramethylpiperidine 1-oxyl and 0.45 g of tetraisopropyl titanate were added. The mixture was heated to 90° C. for approximately 3 hours. Then 150.00 g of the resulting materials was mixed with 350.00 g of cyclopentasiloxane. Nitrogen was bubbled through for 30 minutes. The mixture was stirred and heated to 100° C. Then 0.31 g of dilauroyl peroxide was added. The mixture was stirred for approximately 2 hours at 100° to give a translucent soft solid.

Example 41

Preparation of Silicone Gel XIV 30 g of Functionalized Silicone Network Composition XIII prepared according to Example 40 was mixed with 50 g of cylcopentasiloxane and mixed using an overhead mixer at 600 RPM for 30 minutes. The resulting Silicone Gel XIV had a viscosity of 76,000 centipoise ("cPs") (measured after 24 hours).

Example 42

TABLE XXXIII

Exemplary Structural and Stoichiometric Parameters for Polyether Substituents Affecting Water or Oil Swellability Based on the following formula for the polyether substituent:
$(-CH_2CH(R^9)(R^{10})_nO(R^{11})_o(C_2H_4O)_p(C_3H_6O)_q(C_4H_8O)_rR^{12})$

|  | Water swelling | Oil swelling |
|---|---|---|
| $R^9$ | H, $CH_3$ | H, $CH_3$ |
| $R^{10}$ | $CH_2$ | $CH_2$ |
| $R^{11}$ | None | none |
| $R^{12}$ | H, $CH_3$ | H, $CH_3$, acetyl, butyl |
| n | 1 | 1 |
| o | 0 | 0 |
| p | 11-40 | 5-24 |
| q | 0-27 | 5-27 |
| r | 0 | 0 |
| p/q | >2/3 | |

It is re-emphasized that the preceding ranges of structural parameters and stoichiometric subscripts exemplified for water or oil swellability in Table XXXIII are variable and interdependent and each parametric variable may be exceeded by being greater than or less than the indicated ranges and still observing a particular type of swellability by reason of a homeostatic variation in another structural or stoichiometric parameter associated with the particular polymer.

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all sub-ranges there between. Such ranges may be viewed as a Markush group or groups consisting of differing pairwise numerical limitations which group or groups is or are fully defined by its lower and upper bounds, increasing in a regular fashion numerically and where appropriate integrally from lower bounds to upper bounds. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents (and patent applications) referenced herein are herewith and hereby specifically incorporated by reference in their entirety as though set forth in full.

Having described the invention, that which is claimed is:

1. A cosmetic composition comprising a silicone composition comprising the reaction product of:

a) $M_a M^H_{b-h-k} M^{PE}_h M^E_k D_c D^H_{d-i-l} D^{PE}_i D^E_l T_e T^H_{f-j-m} T^{PE}_j T^E_m Q_g$;

b) a stoichiometric or super-stoichiometric quantity of acrylate where $M = R^1 R^2 R^3 SiO_{1/2}$;

$M^H = R^4 R^5 H SiO_{1/2}$;

$M^{PE} = R^4 R^5 (-CH_2 CH(R^9)(R^{10})_n O(R^{11})_o (C_2 H_4 O)_p (C_3 H_6 O)_q (C_4 H_8 O)_r R^{12}) SiO_{1/2}$;

$M^E = R^4 R^5 (-R^{17} R^{18} C - CR^{16} Q_s Q_t R^{15} (COC) R^{13} R^{14}) SiO_{1/2}$ $D = R^6 R^7 SiO_{2/2}$; and $D^H = R^8 H SiO_{2/2}$ $D^{PE} = R^8 (-CH_2 CH(R^9)(R^{10})_n O(R^{11})_o (C_2 H_4 O)_p (C_3 H_6 O)_q (C_4 H_8 O)_r R^{12}) SiO_{2/2}$ $D^E = R^8 (-R^{17} R^{18} C - CR^{16} Q_s Q_t R^{15} (COC) R^{13} R^{14}) SiO_{2/2}$;

$T = R^{19} SiO_{3/2}$;

$T^H = H SiO_{3/2}$;

$T^{PE} = (-CH_2 CH(R^9)(R^{10})_n O(R^{11})_o (C_2 H_4 O)_p (C_3 H_6 O)_q (C_4 H_8 O)_r R^{12}) SiO_{3/2}$;

$T^E = (-R^{17} R^{18} C - CR^{16} Q_s Q_t R^{15} (COC) R^{13} R^{14}) SiO_{3/2}$; and $Q = SiO_{4/2}$;

where $R^1$, $R^2$, $R^3$, $R^4$, $R^5$, $R^6$, $R^7$, $R^8$ and $R^{19}$ are each independently selected from the group of monovalent hydrocarbon radicals having from 1 to 60 carbon atoms; $R^9$ is H or a 1 to 6 carbon atom alkyl group; $R^{10}$ is a divalent alkyl radical of 1 to 6 carbons;

$R^{11}$ is selected from the group of divalent radicals consisting of $-C_2 H_4 O-$, $-C_3 H_6 O-$, and $-C_4 H_8 O-$; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q_s$ is a divalent hydrocarbon radical having from one to sixty carbon atoms subject to the limitation that when $Q_t$ is trivalent $R^{14}$ is absent and $R^{16}$ and $R^{18}$ may be either cis- or trans- to each other;

the subscript a may be zero or positive subject to the limitation that when the subscript a is zero, b must be positive;

the subscript b may be zero or positive subject to the limitation that when b is zero, the subscript a must be positive;

the subscript c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2 subject to the limitation that the sum of the subscripts h, i and j is positive;

the subscript i is zero or positive and has a value ranging from 0 to about 200 subject to the limitation that the sum of the subscripts h, i and j is positive;

the subscript j is zero or positive and has a value ranging from 0 to about 30 subject to the limitation that the sum of the subscripts h, i and j is positive;

the subscript k is zero or positive and has a value ranging from 0 to about 2 subject to the limitation that the sum of the subscripts k, l and m is positive;

the subscript l is zero or positive and has a value ranging from 0 to about 200 subject to the limitation that the sum of the subscripts k, l and m is positive;

the subscript m is zero or positive and has a value ranging from 0 to about 30 subject to the limitation that the sum of the subscripts k, l and m is positive;

the subscript n is zero or one;

the subscript o is zero or one;

the subscript p is zero or positive and has a value ranging from 0 to about 100 subject to the limitation that (p+q+r)>0;

the subscript q is zero or positive and has a value ranging from 0 to about 100 subject to the limitation that (p+q+r)>0;

the subscript r is zero or positive and has a value ranging from 0 to about 100 subject to the limitation that (p+q+r)>0;

the subscript s is zero or one;

the subscript t is zero or one; and c) a free radical initiator, wherein the reaction product is swellable and said cosmetic composition has an enhanced resistance to syneresis.

2. The composition of claim 1 wherein said silicone composition is self-emulsifying.

3. The composition of claim 1 wherein said silicone composition may be swollen by a solvent.

4. The composition of claim 3 wherein said solvent is water.

5. The composition of claim 3 wherein said solvent is a silicone or an oil.

6. The composition of claim 3 wherein $R^1$, $R^2$, $R^3$, $R^4$, $R^5$, $R^6$, $R^7$, $R^8$ and $R^{19}$ are each methyl.

7. The composition of claim 4 wherein $R^1$, $R^2$, $R^3$, $R^4$, $R^5$, $R^6$, $R^7$, $R^8$ and $R^{19}$ are each methyl.

8. The composition of claim 5 wherein $R^1$, $R^2$, $R^3$, $R^4$, $R^5$, $R^6$, $R^7$, $R^8$ and $R^{19}$ are each methyl.

9. The composition of claim 7 where $R^{17} R^{18} C - CR^{16} Q_s Q_t R^{15} (COC) R^{13} R^{14}$ is vinylcyclohexene oxide.

10. The composition of claim 8 where $R_{17} R^{18} C - CR_{16} Q_s Q_t R^{15} (COC) R^{13} R^{14}$ is vinylcyclohexene oxide.

11. A cosmetic composition comprising an aqueous emulsion where the discontinuous phase comprises water and the continuous phase comprises a silicone composition comprising the reaction product of:

a) $M_a M^H_{b-h-k} M^{PE}_h M^E_k D_c D^H_{d-i-l} D^{PE}_i D^E_l T_e T^H_{f-j-m} T^{PE}_j T^E_m Q_g$;

b) a stoichiometric or super-stoichiometric quantity of acrylate where $M = R^1 R^2 R^3 SiO_{1/2}$;

$M^H = R^4 R^5 H SiO_{1/2}$;

$M^{PE} = R^4 R^5 (-CH_2 CH(R^9)(R^{10})_n O(R^{11})_o (C_2 H_4 O)_p (C_3 H_6 O)_q (C_4 H_8 O)_r R^{12}) SiO_{1/2}$;

$M^E = R^4 R^5 (-R^{17} R^{18} C - CR^{16} Q_s Q_t R^{15} (COC) R^{13} R^{14}) SiO_{1/2}$ $D = R^6 R^7 SiO_{2/2}$; and $D^H = R^8 H SiO_{2/2}$ $D^{PE} = R^8 (-CH_2 CH(R^9)(R^{10})_n O(R^{11})_o (C_2 H_4 O)_p (C_3 H_6 O)_q (C_4 H_8 O)_r R^{12}) SiO_{2/2}$ $D^E = R^8 (-R^{17} R^{18} C - CR^{16} Q_s Q_t R^{15} (COC) R^{13} R^{14}) SiO_{2/2}$;

$T = R^{19} SiO_{3/2}$;

$T^H = H SiO_{3/2}$;

$T^{PE} = (-CH_2 CH(R^9)(R^{10})_n O(R^{11})_o (C_2 H_4 O)_p (C_3 H_6 O)_q (C_4 H_8 O)_r R^{12}) SiO_{3/2}$;

$T^E = (-R^{17}R^{18}C-CR^{16}Q_sQ_tR^{15}(COC)R^{13}R^{14})SiO_{3/2}$; and $Q = SiO_{4/2}$;

where $R^1$, $R^2$, $R^3$, $R^4$, $R^5$, $R^6$, $R^7$, $R^8$ and $R^{19}$ are each independently selected from the group of monovalent hydrocarbon radicals having from 1 to 60 carbon atoms; $R^9$ is H or a 1 to 6 carbon atom alkyl group; $R^{10}$ is a divalent alkyl radical of 1 to 6 carbons;

$R^{11}$ is selected from the group of divalent radicals consisting of $-C_2H_4O-$, $-C_3H_6O-$, and $-C_4H_8O-$; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q_s$ is a divalent hydrocarbon radical having from one to sixty carbon atoms subject to the limitation that when $Q_t$ is trivalent $R^{14}$ is absent and where $R^{16}$ and $R^{18}$ may be either cis- or trans- to each other;

the subscript a may be zero or positive subject to the limitation that when the subscript a is zero, b must be positive;

the subscript b may be zero or positive subject to the limitation that when b is zero, the subscript a must be positive;

the subscript c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2 subject to the limitation that the sum of the subscripts h, i and j is positive;

the subscript i is zero or positive and has a value ranging from 0 to about 200 subject to the limitation that the sum of the subscripts h, i and j is positive;

the subscript j is zero or positive and has a value ranging from 0 to about 30 subject to the limitation that the sum of the subscripts h, i and j is positive;

the subscript k is zero or positive and has a value ranging from 0 to about 2 subject to the limitation that the sum of the subscripts k, l and m is positive;

the subscript l is zero or positive and has a value ranging from 0 to about 200 subject to the limitation that the sum of the subscripts k, l and m is positive;

the subscript m is zero or positive and has a value ranging from 0 to about 30 subject to the limitation that the sum of the subscripts k, l and m is positive;

the subscript n is zero or one;

the subscript o is zero or one;

the subscript p is zero or positive and has a value ranging from 0 to about 100 subject to the limitation that (p+q+r)>0;

the subscript q is zero or positive and has a value ranging from 0 to about 100 subject to the limitation that (p+q+r)>0;

the subscript r is zero or positive and has a value ranging from 0 to about 100 subject to the limitation that (p+q+r)>0;

the subscript s is zero or one; and the subscript t is zero or one; and c) a free radical initiator, wherein said cosmetic composition has an enhanced resistance to syneresis.

12. The composition of claim 11 wherein said silicone composition is self-emulsifying.

13. The composition of claim 11 wherein said silicone composition may be swollen by a solvent.

14. The composition of claim 13 wherein said solvent is water.

15. The composition of claim 13 wherein said solvent is a silicone or an oil.

16. The composition of claim 13 wherein $R^1$, $R^2$, $R^3$, $R^4$, $R^5$, $R^6$ $R^7$, $R^8$ and $R^{19}$ are each methyl.

17. The composition of claim 14 wherein $R^{1, R2}$, $R^3$, $R^4$, $R^5$, $R^6$, $R^7$, $R^8$ and $R^{19}$ are each methyl.

18. The composition of claim 15 wherein $R^1$, $R^2$, $R^3$, $R^4$, $R^5$, $R^6$ $R^7$, $R^8$ and $R^{19}$ are each methyl.

19. The composition of claim 17 where $R^{17}R^{18}C-CR^{16}Q_sQ_tR^{15}(COC)R^{13}R^{14}$ is vinylcyclohexene oxide.

20. The composition of claim 18 where $R^{17}R^{18}C-CR^{16}Q_sQ_tR^{15}(COC)R^{13}R^{14}$ is vinylcyclohexene oxide.

21. A composition comprising an aqueous emulsion where the continuous phase comprises water and the discontinuous phase comprises the reaction product of:

a) $M_a M^H_{b-h-k} M^{PE}_h M^E_k D_c D^H_{d-i-l} D^{PE}_i D^E_l T_e T^H_{f-j-m} T^{PE}_j T^E_m Q_g$;

b) a stoichiometric or super-stoichiometric quantity of acrylate where $M = R^1R^2R^3SiO_{1/2}$;

$M^H = R^4R^5HSiO_{1/2}$;

$M^{PE} = R^4R^5(-CH_2CH(R^9)(R^{10})_nO(R^{11})_o(C_2H_4O)_p(C_3H_6O)_q(C_4H_8O)_rR^{12})SiO_{1/2}$;

$M^E = R^4R^5(-R^{17}R^{18}C-CR^{16}Q_sQ_tR^{15}(COC)R^{13}R^{14})SiO_{1/2}$ $D = R^6R^7SiO_{2/2}$; and $D^H = R^8HSiO_{2/2}$ $D^{PE} = R^8(-CH_2CH(R^9)(R^{10})_nO(R^{11})_o(C_2H_4O)_p(C_3H_6O)_q(C_4H_8O)_rR^{12})SiO_{2/2}$ $D^E = R^8(-R^{17}R^{18}C-CR^{16}Q_sQ_tR^{15}(COC)R^{13}R^{14})SiO_{2/2}$;

$T = R^{19}SiO_{3/2}$;

$T^H = HSiO_{3/2}$;

$T^{PE} = (-CH_2CH(R^9)(R^{10})_nO(R^{11})_o(C_2H_4O)_p(C_3H_6O)_q(C_4H_8O)_rR^{12})SiO_{3/2}$;

$T^E = (-R^{17}R^{18}C-CR^{16}Q_sQ_tR^{15}(COC)R^{13}R^{14})SiO_{3/2}$; and $Q = SiO_{4/2}$;

where $R^1$, $R^2$, $R^3$, $R^4$, $R^5 R^6$, $R^7$, $R^8$ and $R^{19}$ are each independently selected from the group of monovalent hydrocarbon radicals having from 1 to 60 carbon atoms; $R^9$ is H or a 1 to 6 carbon atom alkyl group; $R^{10}$ is a divalent alkyl radical of 1 to 6 carbons;

$R^{11}$ is selected from the group of divalent radicals consisting of $-C_2H_4O-$, $-C_3H_6O-$, and $-C_4H_8O-$; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q_s$ is a divalent hydrocarbon radical having from one to sixty carbon atoms subject to the limitation that when $Q_t$ is trivalent $R^{14}$ is absent and where $R^{16}$ and $R^{18}$ may be either cis- or trans- to each other;

the subscript a may be zero or positive subject to the limitation that when the subscript a is zero, b must be positive;

the subscript b may be zero or positive subject to the limitation that when b is zero, the subscript a must be positive;

the subscript c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2 subject to the limitation that the sum of the subscripts h, i and j is positive;

the subscript i is zero or positive and has a value ranging from 0 to about 200 subject to the limitation that the sum of the subscripts h, i and j is positive;

the subscript j is zero or positive and has a value ranging from 0 to about 30 subject to the limitation that the sum of the subscripts h, i and j is positive;

the subscript k is zero or positive and has a value ranging from 0 to about 2 subject to the limitation that the sum of the subscripts k, l and m is positive;

the subscript l is zero or positive and has a value ranging from 0 to about 200 subject to the limitation that the sum of the subscripts k, l and m is positive;

the subscript m is zero or positive and has a value ranging from 0 to about 30 subject to the limitation that the sum of the subscripts k, l and m is positive;

the subscript n is zero or one;

the subscript o is zero or one;

the subscript p is zero or positive and has a value ranging from 0 to about 100 subject to the limitation that (p+q+r)>0;

the subscript q is zero or positive and has a value ranging from 0 to about 100 subject to the limitation that (p+q+r)>0;

the subscript r is zero or positive and has a value ranging from 0 to about 100 subject to the limitation that (p+q+r)>0;

the subscript s is zero or one;

the subscript t is zero or one; and c) a free radical initiator, wherein said composition has an enhanced resistance to syneresis.

22. The composition of claim 21 wherein said silicone composition is self-emulsifying.

23. The composition of claim 21 wherein said silicone composition may be swollen by a solvent.

24. The composition of claim 23 wherein said solvent is water.

25. The composition of claim 23 wherein said solvent is a silicone or an oil.

26. The composition of claim 23 wherein $R^1$, $R^2$, $R^3$, $R^4$, $R^5$, $R^6$, $R^7 R^8$ and $R^{19}$ are each methyl.

27. The composition of claim 24 wherein $R^1$, $R^2$, $R^3$, $R^4$, $R^5$, $R^6$, $R^7$, $R^8$ and $R^{19}$ are each methyl.

28. The composition of claim 25 wherein $R^1$, $R^2$, $R^3$, $R^4$, $R^5$, $R^6$, $R^7$, $R^8$ and $R^{19}$ are each methyl.

29. The composition of claim 27 where $R^{17}R^{18}C—CR^{16}Q_sQ_tR^{15}(COC)R^{13}R^{14}$ is vinylcyclohexene oxide.

30. The composition of claim 28 where $R^{17}R^{18}C—CR^{16}Q_sQ_tR^{15}(COC)R^{13}R^{14}$ is vinylcyclohexene oxide.

31. A cosmetic composition comprising a non-aqueous emulsion where the discontinuous phase comprises a non-aqueous hydroxylic solvent and the continuous phase comprises the reaction product of:

a) $M_aM^H_{b-h-k}M^{PE}_hM^E_kD_cD^H_{d-i-l}D^{PE}_iD^E_lT_eT^H_{f-j-m}T^{PE}_jT^E_mQ_g$;

b) a stoichiometric or super-stoichiometric quantity of acrylate where $M=R^1R^2R^3SiO_{1/2}$;

$M^H=R^4R^5HSiO_{1/2}$;

$M^{PE}=R^4R^5(—CH_2CH(R^9)(R^{10})_nO(R^{11})_o(C_2H_4O)_p(C_3H_6O)_q(C_4H_8O)_rR^{12})SiO_{1/2}$;

$M^E=R^4R^5(—R^{17}R^{18}C—CR^{16}Q_sQ_tR^{15}(COC)R^{13}R^{14})SiO_{1/2}$ $D=R^6R^7SiO_{2/2}$; and $D^H=R^8HSiO_{2/2}$ $D^{PE}=R^8(—CH_2CH(R^9)(R^{10})_nO(R^{11})_o(C_2H_4O)_p(C_3H_6O)_q(C_4H_8O)_rR^{12})SiO_{2/2}$ $D^E=R^8(—R^{17}R^{18}C—CR^{16}Q_sQ_tR^{15}(COC)R^{13}R^{14})SiO_{2/2}$;

$T=R^{19}SiO_{3/2}$;

$T^H=HSiO_{3/2}$;

$T^{PE}=(—CH_2CH(R^9)(R^{10})_nO(R^{11})_o(C_2H_4O)_p(C_3H_6O)_q(C_4H_8O)_rR^{12})SiO_{3/2}$;

$T^E=(—R^{17}R^{18}C—CR^{16}Q_sQ_tR^{15}(COC)R^{13}R^{14})SiO_{3/2}$; and $Q=SiO_{4/2}$;

where $R^1$, $R^2$, $R^3$, $R^4$, $R^5$, $R^6$, $R^7$, $R^8$ and $R^{19}$ are each independently selected from the group of monovalent hydrocarbon radicals having from 1 to 60 carbon atoms;

$R^9$ is H or a 1 to 6 carbon atom alkyl group; $R^{10}$ is a divalent alkyl radical of 1 to 6 carbons;

$R^{11}$ is selected from the group of divalent radicals consisting of $—C_2H_4O—$, $—C_3H_6O—$, and $—C_4H_8O—$; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q_s$ is a divalent hydrocarbon radical having from one to sixty carbon atoms subject to the limitation that when $Q_t$ is trivalent $R^{14}$ is absent and where $R^{16}$ and $R^{18}$ may be either cis- or trans- to each other;

the subscript a may be zero or positive subject to the limitation that when the subscript a is zero, b must be positive;

the subscript b may be zero or positive subject to the limitation that when b is zero, the subscript a must be positive;

the subscript c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2 subject to the limitation that the sum of the subscripts h, i and j is positive;

the subscript i is zero or positive and has a value ranging from 0 to about 200 subject to the limitation that the sum of the subscripts h, i and j is positive;

the subscript j is zero or positive and has a value ranging from 0 to about 30 subject to the limitation that the sum of the subscripts h, i and j is positive;

the subscript k is zero or positive and has a value ranging from 0 to about 2 subject to the limitation that the sum of the subscripts k, l and m is positive;

the subscript l is zero or positive and has a value ranging from 0 to about 200 subject to the limitation that the sum of the subscripts k, l and m is positive;

the subscript m is zero or positive and has a value ranging from 0 to about 30 subject to the limitation that the sum of the subscripts k, l and m is positive;

the subscript n is zero or one;

the subscript o is zero or one;

the subscript p is zero or positive and has a value ranging from 0 to about 100 subject to the limitation that $(p+q+r)>0$;

the subscript q is zero or positive and has a value ranging from 0 to about 100 subject to the limitation that $(p+q+r)>0$;

the subscript r is zero or positive and has a value ranging from 0 to about 100 subject to the limitation that $(p+q+r)>0$;

the subscript s is zero or one;

the subscript t is zero or one; and c) a free radical initiator, wherein said composition has an enhanced resistance to syneresis.

32. The composition of claim 31 wherein said silicone composition is self-emulsifying.

33. The composition of claim 31 wherein said silicone composition may be swollen by a solvent.

34. The composition of claim 33 wherein said solvent is water.

35. The composition of claim 33 wherein said solvent is a silicone or an oil.

36. The composition of claim 33 wherein $R^1$, $R^2$, $R^3$, $R^4$, $R^5$, $R^6$, $R^7$, $R^8$ and R19 are each methyl.

37. The composition of claim 34 wherein $R^{1, R2}$, $R^3$, $R^4$, $R^5$, $R^6$, $R^7$, $R^8$ and $R^{19}$ are each methyl.

38. The composition of claim 35 wherein $R^1$, $R^2$, $R^3$, $R^4$, $R^5$, $R^6$, $R^7$, $R^8$ and $R^{19}$ are each methyl.

39. The composition of claim 37 where $R^{17}R^{18}C-CR^{16}Q_sQ_tR^{15}(COC)R^{13}R^{14}$ is vinylcyclohexene oxide.

40. The composition of claim 38 where $R^{17}R^{18}C-CR^{16}Q_sQ_tR^{15}(COO)R^{13}R^{14}$ is vinylcyclohexene oxide.

41. A cosmetic composition comprising a non-aqueous emulsion where the continuous phase comprises a non-aqueous hydroxylic organic solvent and the discontinuous phase comprises the reaction product of:

a) $M_aM^H_{b-h-k}M^{PE}_hM^E_kD_cD^H_{d-i-l}D^{PE}_iD^E_lT_eT^H_{f-j-m}T^{PE}_jT^E_mQ_g$;

b) a stoichiometric or super-stoichiometric quantity of acrylate where $M=R^1R^2R^3SiO_{1/2}$;

$M^H=R^4R^5HSiO_{1/2}$;

$M^{PE}=R^4R^5(-CH_2CH(R^9)(R^{10})_nO(R^{11})_o(C_2H_4O)_p(C_3H_6O)_q(C_4H_8O)_rR^{12})SiO_{1/2}$;

$M^E=R^4R^5(-R^{17}R^{18}C-CR^{16}Q_sQ_tR^{15}(COC)R^{13}R^{14})SiO_{1/2}$;

$D=R^6R^7SiO_{2/2}$; and $D^H=R^8HSiO_{2/2}$ $D^{PE}=R^8(-CH_2CH(R^9)(R^{10})_nO(R^{11})_o(C_2H_4O)_p(C_3H_6O)_q(C_4H_8O)_rR^{12})SiO_{2/2}$ $D^E=R^8(-R^{17}R^{18}C-CR^{16}Q_sQ_tR^{15}(COC)R^{13}R^{14})SiO_{2/2}$;

$T=R^{19}SiO_{3/2}$;

$T^H=HSiO_{3/2}$;

$T^{PE}=(-CH_2CH(R^9)(R^{10})_nO(R^{11})_o(C_2H_4O)_p(C_3H_6O)_q(C_4H_8O)_rR^{12})SiO_{3/2}$;

$T^E=(-R^{17}R^{18}C-CR^{16}Q_sQ_tR^{15}(COC)R^{13}R^{14})SiO_{3/2}$; and $Q=SiO_{4/2}$;

where $R^1$, $R^2$, $R^3R^4$, $R^5R^6$, $R^7$, $R^8$ and $R^{19}$ are each independently selected from the group of monovalent hydrocarbon radicals having from 1 to 60 carbon atoms;

$R^9$ is H or a 1 to 6 carbon atom alkyl group; $R^{10}$ is a divalent alkyl radical of 1 to 6 carbons;

$R^{11}$ is selected from the group of divalent radicals consisting of $-C_2H_4O-$, $-C_3H_6O-$, and $-C_4H_8O-$; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q_s$ is a divalent hydrocarbon radical having from one to sixty carbon atoms subject to the limitation that when $Q_t$ is trivalent $R^{14}$ is absent and where $R^{16}$ and $R^{18}$ may be either cis- or trans- to each other;

the subscript a may be zero or positive subject to the limitation that when the subscript a is zero, b must be positive;

the subscript b may be zero or positive subject to the limitation that when b is zero, the subscript a must be positive;

the subscript c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2 subject to the limitation that the sum of the subscripts h, i and j is positive;

the subscript i is zero or positive and has a value ranging from 0 to about 200 subject to the limitation that the sum of the subscripts h, i and j is positive;

the subscript j is zero or positive and has a value ranging from 0 to about 30 subject to the limitation that the sum of the subscripts h, i and j is positive;

the subscript k is zero or positive and has a value ranging from 0 to about 2 subject to the limitation that the sum of the subscripts k, l and m is positive;

the subscript l is zero or positive and has a value ranging from 0 to about 200 subject to the limitation that the sum of the subscripts k, l and m is positive;

the subscript m is zero or positive and has a value ranging from 0 to about 30 subject to the limitation that the sum of the subscripts k, l and m is positive;

the subscript n is zero or one;

the subscript o is zero or one;

the subscript p is zero or positive and has a value ranging from 0 to about 100 subject to the limitation that $(p+q+r)>0$;

the subscript q is zero or positive and has a value ranging from 0 to about 100 subject to the limitation that $(p+q+r)>0$;

the subscript r is zero or positive and has a value ranging from 0 to about 100 subject to the limitation that (p+q+r)>0;

the subscript s is zero or one;

the subscript t is zero or one; and c) a free radical initiator, wherein said composition has an enhanced resistance to syneresis.

42. The composition of claim 41 wherein said silicone composition is self-emulsifying.

43. The composition of claim 41 wherein said silicone composition may be swollen by a solvent.

44. The composition of claim 43 wherein said solvent is water.

45. The composition of claim 43 wherein said solvent is a silicone or an oil.

46. The composition of claim 43 wherein $R^1$, $R^2$, $R^3$, $R^4$ $R^5$, $R^6$, $R^7$, $R^8$ and $R^{19}$ are each methyl.

47. The composition of claim 44 wherein $R^1$, $R^2$, $R^3$, $R^4$, $R^5$, $R^6$, $R^7$, $R^8$ and $R^{19}$ are each methyl.

48. The composition of claim 45 wherein $R^1$, $R^2$, $R^3$, $R^4$, $R^5$, $R^6$, $R^7$, $R^8$ and $R^{19}$ are each methyl.

49. The composition of claim 47 where $R^{17}R^{18}C$—$CR^{16}Q_sQ_tR^{15}$ $(COC)R^{13}R^{14}$ is vinylcyclohexene oxide.

50. The composition of claim 48 where $R^{17}R^{18}C$—$CR^{16}Q_sQ_tR^{15}$ $(COC)R^{13}R^{14}$ is vinylcyclohexene oxide.

51. An oil-in-water emulsion comprising the composition of claim 1 wherein said composition is present in the water phase.

52. A water-in-oil emulsion comprising the composition of claim 1 wherein said composition is present in the water phase.

53. A non-aqueous emulsion where the discontinuous phase comprises a non-aqueous hydroxylic organic solvent and the composition of claim 1.

54. A non-aqueous emulsion where the continuous phase comprises a non-aqueous hydroxylic organic solvent and the composition of claim 1.

* * * * *